US010017527B2

(12) United States Patent
Joossens et al.

(10) Patent No.: US 10,017,527 B2
(45) Date of Patent: Jul. 10, 2018

(54) KLK4 INHIBITORS

(71) Applicant: Universiteit Antwerpen, Antwerp (BE)

(72) Inventors: Jurgen Joossens, Zoersel (BE); Koen Augustyns, Hoogstraten (BE); Anne-Marie Lambeir, Leuven (BE); Pieter Van Der Veken, Sint-Katelijne-Waver (BE); Jeroen Van Soom, Antwerpen (BE); Viktor Magdolen, Munich (DE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 0 days.

(21) Appl. No.: 15/128,446

(22) PCT Filed: Mar. 30, 2015

(86) PCT No.: PCT/EP2015/056908
§ 371 (c)(1),
(2) Date: Sep. 23, 2016

(87) PCT Pub. No.: WO2015/144933
PCT Pub. Date: Oct. 1, 2015

(65) Prior Publication Data
US 2017/0101427 A1 Apr. 13, 2017

(30) Foreign Application Priority Data

Mar. 28, 2014 (EP) ..................... 14162227

(51) Int. Cl.
C07F 9/6561 (2006.01)
C07F 9/40 (2006.01)
A61K 49/00 (2006.01)
C07F 9/58 (2006.01)
C07F 9/655 (2006.01)
C07F 9/6553 (2006.01)
C07F 9/6509 (2006.01)
C07F 9/6558 (2006.01)
C12Q 1/37 (2006.01)

(52) U.S. Cl.
CPC ........ *C07F 9/6561* (2013.01); *A61K 49/0052* (2013.01); *C07F 9/4087* (2013.01); *C07F 9/588* (2013.01); *C07F 9/65515* (2013.01); *C07F 9/65583* (2013.01); *C07F 9/65586* (2013.01); *C07F 9/650988* (2013.01); *C07F 9/655345* (2013.01); *C12Q 1/37* (2013.01); *G01N 2333/96433* (2013.01)

(58) Field of Classification Search
CPC ................... C07F 9/6561; A61K 49/0052
See application file for complete search history.

(56) References Cited

U.S. PATENT DOCUMENTS 8,003,627 B2 * 8/2011 Augustyns ............ C07F 9/4006
514/119

FOREIGN PATENT DOCUMENTS

EP 2676962 A1 12/2013
WO WO/02077243 A1 10/2002
WO WO/2005083110 A1 9/2005
WO WO2007045496 A1 4/2007
WO WO2012152807 A1 11/2012

OTHER PUBLICATIONS

Augustyns et al (2007): STN International HCAPLUS database, (Columbus, Ohio), Accession No. 2007:463391.*
Grzywa et al., "The molecular basis of urokinase inhibition: from the nonempirical analysis of intermolecular interactions to the prediction of binding affinity", Journal of Molecular Modeling, Springer, DE, vol. 13, No. 6-7, Mar. 20, 2007, pp. 677-683, XP019520060, ISSN: 0948-5023, DOI:10.1007/S00894-007-0193-8.
Joossens et aL, "Development of Irreversible Diphenyl Phosphonate Inhibitors for Urokinase Plasminogen Activator", Journal of Medicinal Chemistry, American Chemical Society, US, vol. 47, No. 10, Jan. 1, 2004; pp. 2411-2413, XP002422331, ISSN: 0022-2623, DOI: 10.1021/JM0499209.
Sienczyk et al, "Inhibition of trypsin and urokinase by Cbz-amino (4-guanidinophenyl) methanephosphonate aromatic ester derivatives: The influence of the ester group on their biological activity", Bioorganic & Medicinal Chemistry Letters, Pergamon, Amsterdam, NL, vol. 16, No. 11, Jun. 1, 2006, pp. 2886-2890, XP027965510, ISSN: 0960-894X.
Sienczyk et al., "New potent cathepsin G phosphonate inhibitors", Bioorganic & Medicinal Chemistry, Pergamon, GB, vol. 16, No. 19, Oct. 1, 2008, pp. 8863-8867, XP025468943, ISSN: 0968-0896, DOI: 10.1016/J.BMC.2008.08.069.
International Search Report and Written Opinion completed Jul. 10, 2015, pertaining to PCT/EP2015/056908 filed Mar. 30, 2015.
Sienczyk et al., "A convenient synthesis of new alpha-aminoalkylphosphonates, aromatic analogues of arginine as inhibitors of trypsin-like enzymes", Tetrahedron Letters 45(39); 2004; pp. 7251-7254.
Blum et al., "Comparative Assessment of Substrates and Activity Based Probes as Tools for Non-Invasive Optical Imaging of Cysteine Protease Activity", Plos One 4(7); 2009; pp. 1-10.
Pan et al. "Development of activity-based probes for trypsin-family serine proteases", Bioorganic & Medicinal Chemistry Letters 16(11); 2006; pp. 2882-2885.
Lambeir et al., "Dipeptide-derived diphenyl phosphonate esters: mechanism-based inhibitors of dipeptidyl peptidase IV", Biochimica et Biophysica Acta (BBA)—General Subjects 1290(1); 1996; pp. 76-82.
Schmitt et al., "Emerging clinical importance of the cancer biomarkers kallikrein-related peptidases (KLK) in female and male reproductive organic malignancies", Radiology and Oncology 47(4); 2013; pp. 319-329.

(Continued)

*Primary Examiner* — Golam M Shameem
(74) *Attorney, Agent, or Firm* — Dinsmore & Shohl LLP

(57) ABSTRACT

The present invention relates to novel compounds and probes which have a common chemical structure necessary to obtain potent inhibitory activity against KLK4 and/or may be used for the detection of KLK4 peptides and their activity. It further relates to the use of these compounds and methods for inhibiting and/or detecting KLK4 activity in vitro and in vivo by making use of said probes or inhibitors. The compounds of the invention differ from prior art compounds at least in the presence of phenyl guanidine (instead of e.g. benzyl guanidine) and/or the presence of a heteroatom in the tail group, their combined presence unexpectedly leading to potent and selective KLK4 inhibitory activity.

11 Claims, No Drawings

(56) References Cited

OTHER PUBLICATIONS

Dikonomopoulou et al., "Immunofluorometric activity-based probe analysis of active KLK6 in biological fluids", Biological Chemistry 389(6); 2008; pp. 747-756.
Sienczyk et al., "Irreversible Inhibition of Serine Proteases—Design and In-Vivo Activity of Diaryl alpha-Aminophosphonate Derivatives", Current Medicinal Chemistry (16(13); 2009; pp. 1673-1687.
Van Der Veken et al., "Lewis Acid Catalyzed Synthesis of N-Protected Diphenyl 1-Aminoalkylphosphonates", Syntheses: Journal of synthetic organic chemistry; 2005; pp. 634-638.
Goettig et al., "Natural and synthetic inhibitors of kallikrein-related peptidases (KLKs)", Biochimie 92(11); 2010; pp. 1546-1567.
Brown et al., "Peptide Length and Leaving-Group Sterics Influence Potency of Peptide Phosphonate Protease Inhibitors", Chemistry & Biology 18(1); 2011; pp. 48-57.
Jung et al., "Practical syntheses of dyes for difference gel electronphoresis", Bioorganic & Medicinal Chemistry 14(1); 2006; pp. 92-97.
Joossens et al., "Small, Potent, and Selective Diaryl Phosphonate Inhibitors for Urokinase-Type Plasminogen Activator with In Vivo Antimetastatic Properties", Journal of Medicinal Chemistry 50(26); 2007; pp. 6638-6646.
Drag et al., "Synthesis of alpha(1)-(Cbz-aminoalkyl)-alpha 2-(hydroxyalkyl)phosphinic esters", Tetrahedron Letters 46 (19); 2005; pp. 3359-3362.
Nguyen et al., "Practical Synthetic Route to Functionalized Rhodamine Dyes", Organic Letters, 2003 vol. 5, No. 18, pp. 3245-3248.
Haedke et al., "Tuning probe selectivity for chemical proteomics applications", Current Opinion in Chemical Biology, 17(1); 2013; pp. 102-109.
Drag et al., "alpha-aminoalkylphosphonates induced apoptosis in human tumor cell lines", Polish Journal of Chemistry, 79(3), pp. 593-602 (2005).
Nguyen et al., "Practical Synthetic Route to Functionalized Rhodarnine Dyes", Organic Letters, 2003 vol. 5, No. 18, pp. 3245-3248.

* cited by examiner

KLK4 INHIBITORS

FIELD OF THE INVENTION

The present invention relates to novel compounds and probes which have a common chemical structure necessary to obtain potent inhibitory activity against KLK4 and/or may be used for the detection of KLK4 peptides and their activity. It further relates to the use of these compounds and methods for inhibiting and/or detecting KLK4 activity in vitro and in vivo by making use of said probes or inhibitors. The compounds of the invention differ from prior art compounds at least in the presence of phenyl guanidine (instead of e.g. benzyl guanidine) and/or the presence of a heteroatom in the tail group, their combined presence unexpectedly leading to potent and selective KLK4 inhibitory activity.

BACKGROUND TO THE INVENTION

The serine proteases of the trypsin-like family play critical roles in many key biological processes including digestion, blood coagulation, and immunity. Moreover, many serine proteases are involved in diseases such as cancer, wound healing, arthritis, skin diseases, ALS, infection, . . . . All the members of the S1 family have a similar protein fold with a catalytic site consisting of the oxyanion hole and critically important Ser, His and Asp amino acids (the catalytic triad). Typically, the members of this family have a S1 pocket, with at the bottom of this pocket a negatively charged Asp residue.

Kallikrein-related peptidases (KLKs) represent a family of fifteen mammalian serine proteases. KLKs are novel cancer biomarkers. KLKs are of clinical value to identify low- versus high-risk cancer patients, and to predict the course of the cancer disease and response to cancer therapeutics of male and female patients afflicted with reproductive tract malignancies, in addition to cancers of the lung, brain, skin, head and neck, kidney, urinary bladder, and the gastrointestinal tract. Especially in high-risk cancer patient groups, these proteases cannot only be biomarkers for prognosis and therapy response but also act as valuable targets for cancer therapeutics, eventually resulting in reduction of the process of tumor cell dissemination and metastasis.

KLK4 is implicated in cardiovascular diseases, cancer, endocrino-logical diseases, metabolic diseases, gastroenterological diseases, inflammation, hemato-logical diseases, respiratory diseases, neurological diseases, reproduction disorders and urological diseases (WO2005083110). Following Schmitt et al. (2013), Kallikrein-related peptidase 4 (KLK4) is a trypsin-like serine protease displaying arginine/lysine-specific protease activity, with a strong preference for Arg at the P1 position of substrates. In general, KLK4 shares several substrates with other members of the KLK family. The KLK4 gene, also known as prostase or KLK-L1, was initially deemed to be expressed exclusively in the prostate, based on Northern blotting data; however, subsequent studies using RT-PCR demonstrated that KLK4 transcripts are also detected in other tissues, including the testes, mammary glands, adrenals, uterus, thyroid, and salivary glands, although at much lower levels. Notably, KLK4 mRNA overexpression was observed in ovarian carcinoma and shown to constitute an independent indicator of poor prognosis in patients with well or moderately differentiated ovarian tumors. KLK4 gene transcription is also elevated in prostate cancer, compared to normal prostatic epithelium and benign prostatic hyperplasia. As described in WO02077243, KLK4 is implicated in hormone-associated carcinomas, such as breast and prostate cancer. Moreover, KLK4 mRNA expression is an unfavorable prognostic predictor in breast cancer patients. According to the results of a recent study, KLK4 may represent a novel endogenous activator of protease-activated receptor 1 (PAR1), as KLK4 was shown to be aberrantly expressed in colonic tumors and capable of inducing PAR1 signaling in HT-29 colorectal adenocarcinoma cells, thus promoting ERK1/2 activation (Schmitt, Magdolen et al. 2013). Furthermore, KLK4 activates protease activated receptor 2 (PAR2) (Blaber et al. 2010), an activator of inflammatory pathways. As such, KLK4 is a target for the treatment of inflammatory diseases.

The overexpression of KLK4 in the mentioned tumor types clearly demonstrates that KLK4 is a therapeutic target for new drugs.

In 2008 Oikonomopoulou at al. reported a tool using a peptidic activity-based probe coupled antibody capture (Oikonomopoulou, Hansen et al. 2008). The probe was built around a pro-lys peptidic fragment which was responsible for the recognition of kallikrein 6. Experts in the field will agree that the antibody approach was needed to cope with the selectivity problems related to the probe described by Oikonomopoulou et al. The probe was earlier described by Pan et al. (Pan, Jeffery et al. 2006). This article clearly showed the non-selectivity of the probes. The apparent affinity Ki(app) for tryptase, trypsin, thrombin and plasmin was in the same order of magnitude (0.6 to 6 µM). The authors clearly stated that the incorporation of a proline residue increased the overall reactivity compared to single amino acid Lys probe. However, this was only a moderate activity increase with no change in the selectivity profile. A more recent publication by Brown et al. reports the synthesis and evaluation of phosphonate ABPs targeting matriptase and thrombin. Both are members of the trypsin fold family of S1A proteases (Brown, Ray et al. 2011). The authors stated that for designing broad-specificity phosphonate ABPs or specific S1A protease ABPs a peptide sequence is required. Additionally the leaving group of the phosphonate peptide sequence, peptide length and peptide stability are marked as key elements for enhancing potency. The most potent peptide containing probe has an $IC_{50}$ value for matriptase of 0.066 mM and a kapp of 490 $M^{-1}S^{-1}$, which is rather modest. Moreover, the $IC_{50}$ values of the presented probes are obtained after a long pre-incubation period (4 hours), which emphasizes the slow reaction characteristics.

Most of the small molecule inhibitors that have been employed in biochemical studies of KLKs are often of insufficient potency and/or specificity. Thus, more potent and selective drug like inhibitors are needed (Goettig, Magdolen et al. 2010).

In the above-mentioned context, it is generally recognized that a chemical which could visualize or capture KLK4 catalytic activity on a qualitative and quantitative manner in in vitro and in vivo settings will be highly useful for different non-clinical and clinical applications (Blum, Weimer et al. 2009). The compounds of the present invention allow such a therapeutic and diagnostic (biomarker) application.

The present invention provides the required chemical template (phenyl guanidine, diphenyl phosphonate and specific tail containing a heteroatom) which is a necessity to obtain selective and potent (preferably irreversibly) binding inhibitors or activity based probes directed towards KLK4.

Previously, no diphenyl phosphonate KLK4 inhibitors were reported. A closely relating compound is compound 5a which was originally reported by Sieniczyk et al., 2006 as a uPA inhibitor with limited potency.

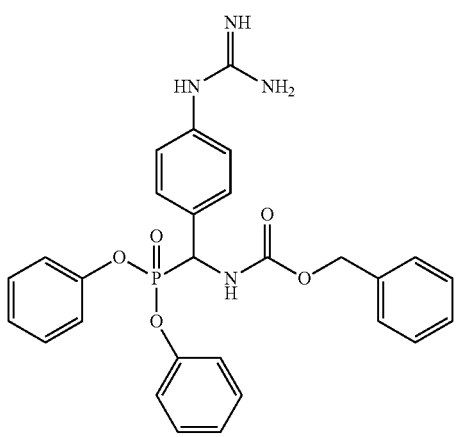

Compound 5a

We have now surprisingly found that compound 5a is a potent KLK4 inhibitor, however the selectivity profile is not optimal because it inhibits also KLK8, KLK2 and KLK1 (see table 2). Moreover compound 5a shows a reversible binding mechanism against KLK4 instead of the theoretically expected irreversible binding mechanism due to the diphenyl phosphonate group. The described invention under this new patent application is related to further structural improvements to obtain more selective compounds and/or switching the reversible mode of binding towards an irreversible one. These improvements can be pointed to the ideal combination of the phenylguanidinyl moiety with the optimal $R_3$ group. In particular, it was found that the incorporation of a heteroatom, with at least 4 atoms located between the heteroatom and the nitrogen to which $R_3$ is attached, delivered potent irreversible KLK4 inhibitors. In compound 5a such heteroatom is not present at this position, and this compound was found to be a reversible, instead of an irreversible KLK4 inhibitor.

Another series of diphenyl phosphonates described originally by Joossens et al., 2007 belongs to the benzylguanidinyl series which show very potent and irreversible uPA binding (see also WO 2007045496). Nevertheless, we found recently that these compound series are also responsible for potent KLK4, KLK8, KLK2 and matriptase binding (compounds uPA1 and uPA2 of table 2). We understand that this binding profile is very interesting to investigate the potential of those compounds as an anti-cancer drugs, but in general drug developers aim for high selectivity towards the selected target.

The presented compounds in this invention are the first reported diphenyl phosphonate KLK4 inhibitors that show an improved selectivity profile with no potent inhibition against uPA, KLK8, and matriptase. Moreover, we have identified novel compounds which show an irreversible KLK4 binding mode, which seems not evident to obtain within this series, because most compounds are unexpectedly reversible binders. The high selectivity profile of these compounds is very important in their use as activity based probes towards KLK4.

SUMMARY OF THE INVENTION

The inventors of the present application have surprisingly found that compounds of formula I are potent inhibitors of KLK4. Moreover, the compounds of the invention display strong selectivity towards KLK4 over other kallikreins and other peptidases. The compounds of the invention are characterized by the presence of a diphenyl phosphonate group (herein also termed 'warhead'), a phenylguanidine group, and a tail (herein also sometimes referred to as a linker) that comprises a heteroatom. It has been found that the simultaneous presence of the phenyl guanidine group and the heteroatom in the tail are required for strong and selective KLK4 inhibition. It has also been identified that potency and selectivity may be improved even further by the selective positioning of a heteroatom in the tail. This allows for irreversible binding of the inhibitors.

In addition, it has been found that a detectable label can be attached to the tail without destroying the KLK4 binding capacity. When the compounds of the invention comprise such a detectable label, they can be used for the detection of KLK4, for example in the diagnostics of cancer.

Therefore, in a first aspect, the invention provides compound of formula I or a stereoisomer, tautomer, racemic, salt, hydrate, or solvate thereof,

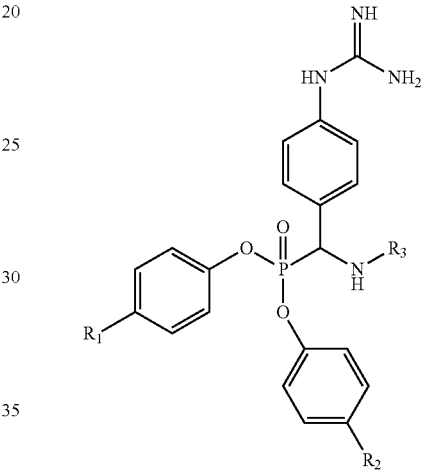

I

Wherein $R_1$ and $R_2$ are each independently —H, —R', —$C_{1-6}$alkyl, —$C_{1-6}$alkenyl, or —$C_{1-6}$alkynyl; wherein said —$C_{1-6}$alkyl, —$C_{1-6}$alkenyl, and —$C_{1-6}$alkynyl is optionally substituted with one or more R' groups and wherein optionally one carbon atom in said —$C_{1-6}$alkyl, —$C_{1-6}$alkenyl, and —$C_{1-6}$alkynyl is replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

$R_3$ is —C(=O)OR$_4$, —C(=O)NR"R$_5$, —S(=O)(=O)R$_6$, —C(=O)R$_7$, or R$_8$;

$R_4$, $R_5$, $R_6$, $R_7$, and $R_8$ are L$_1$-Cy-L$_2$-Det;

$L_1$ is a direct bond or an optionally substituted group selected from —$C_{1-20}$alkyl, —$C_{1-20}$alkenyl, and —$C_{1-20}$alkynyl; wherein said —$C_{1-20}$alkyl-, —$C_{1-20}$alkenyl-, and —$C_{1-20}$alkynyl- is optionally substituted with one or more R' groups, and wherein optionally one or more non-adjacent carbon atoms in said —$C_{1-20}$alkyl-, —$C_{1-20}$alkenyl-, or —$C_{1-20}$alkynyl- are replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

Cy is selected form a direct bond, cycloalkyl, heterocyclyl, aryl, and heteroaryl; wherein said cycloalkyl, heterocyclyl, aryl, and heteroaryl is optionally substituted with one or more R' groups;

L$_2$ is a direct bond or an optionally substituted group selected from —$C_{1-20}$alkyl, —$C_{1-20}$alkenyl, and —$C_{1-20}$ alkynyl; wherein said —$C_{1-20}$alkyl-, —$C_{1-20}$alkenyl-, and —$C_{1-20}$alkynyl- is optionally substituted with one or more R' groups, and wherein optionally one or more non-adjacent carbon atoms in said —$C_{1-20}$alkyl-, —$C_{1-20}$alkenyl-, or —$C_{1-20}$alkynyl- are replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

Det is hydrogen or a detectable label;

R' is each independently selected from the group consisting of amino, hydroxyl, thiol, cyano, nitro, oxo, and halo;

R" is at each instance each independently selected from hydrogen and $C_{1-6}$alkyl;

wherein at least one heteroatom is present in -L$_1$-Cy-L$_2$-;

wherein R$_7$ is not directly attached to the carbonyl through one of the following optionally substituted groups: —N—, —O—, triazole, or an amino acid;

wherein R$_8$ is not directly attached to the amine through one of the following optionally substituted groups: —S(=O)(=O)—, or —C(=O)—; and wherein R$_7$ is not —CH$_2$—O-phenyl.

Viewed from a further aspect, the invention provides a (pharmaceutical and/or veterinary) composition comprising a compound of the invention. Viewed from a still further aspect, the invention provides a compound of the invention for use as a medicine.

Viewed from a still further aspect, the invention provides the use of a compound of the invention in the preparation of a medicament for the prevention and/or treatment of at least one disease and/or disorder selected from cancer and an inflammatory disease.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

As already mentioned hereinbefore, in a first aspect the present invention provides compounds of Formula I

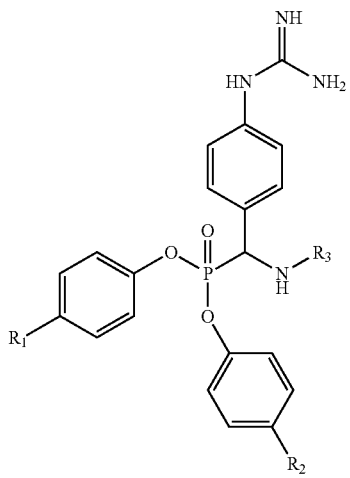

I

Wherein R$_1$, R$_2$ and R$_3$ are as defined hereinbefore, including the stereo-isomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl (also shortened as Me), ethyl, n-propyl (also shortened as nPr), i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like.

The term "alkynyl", as used herein, unless otherwise indicated, means straight-chain or branched-chain hydrocarbon radicals containing at least one carbon-carbon triple bond. Examples of alkynyl radicals include ethynyl, propynyl, isopropynyl, butynyl, isobutynyl, pentynyl, hexynyl, and the like.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

The term heteroatom refers to any atom other than C or H, and may include N, S, O, F, Cl, Br, . . . .

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclyl refers to a heterocyclyl having optionally one or more substituents (for example 1 to 4 substituents, or for example 1, 2, 3 or 4), selected from those defined for substituted aryl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cycloheptenyl, and 1-, 2-, 3-, 4-, or 5-pyrenyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "oxo" as used herein refers to the group =O.

The term "halo" or "halogen" as a group or part of a group is generic for fluoro, chloro, bromo, or iodo. Whenever the term "substituted" is used in the present invention, it is meant to indicate that one or more hydrogens on the atom indicated in the expression using "substituted" is replaced with a selection from the indicated group, provided that the indicated atom's normal valency is not exceeded. As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

The 'detectable label' as used in the context of this invention is meant to include a signal producing group that produces a direct or indirect instrumentally detectable signal and may be any suitable group known in the art. In particular, the detectable label according to the invention is meant to be a group that can be instrumentally detected by a method selected from the list comprising magnetic resonance imaging, X-ray imaging, ultrasound, nuclear medicine imaging, multimodal imaging, fluorescence imaging, bioluminescence imaging, microscopy, mass detectors, wave length detectors, phosphorescent imaging, chemiluminescent imaging, and the like. The presence of said detectable label, allows for the visualization and/or detection of the compounds according to this invention. In particular the detectable label may be selected from the group comprising radio-isotopes, fluorophores, imaging agents for MRI (i.e. paramagnetic metal), X-ray responsive agents, and biotin labels or derivatives thereof. In a preferred embodiment, the detectable label is a directly detectable label, such as but not limited to: biotin, rhodamin, Cy-dyes, metal containing DOTA, groups containing $^{18}F$, $^{11}C$, $^{13}H$ and close analogues Suitable radio-isotopes, may be selected from the list comprising $^{3}H$, $^{11}C$, $^{13}N$, $^{15}O$, $^{18}F$, $^{51}Cr$, $^{52}Fe$, $^{52m}Mn$, $^{55}Co$, $^{60}Cu$, $^{61}Cu$, $^{62}Zn$, $^{62}Cu$, $^{63}Zn$, $^{64}Cu$, $^{66}Ga$, $^{67}Ga$, $^{68}Ga$, $^{70}As$, $^{71}As$, $^{72}As$, $^{74}As$, $^{75}Se$, $^{75}Br$, $^{76}Br$, $^{77}Br$, $^{80m}Br$, $^{82m}Br$, $^{82}Rb$, $^{86}Y$, $^{88}Y$, $^{89}Sr$, $^{89}Zr$, $^{97}Ru$, $^{99m}Tc$, $^{110}In$, $^{111}In$, $^{113m}In$, $^{114m}In$, $^{117m}Sn$, $^{120}I$, $^{122}Xe$, $^{123}I$, $^{124}I$, $^{125}I$, $^{166}Ho$, $^{167}Tm$, $^{169}Yb$, $^{193m}Pt$, $^{195m}Pt$, $^{201}Tl$, $^{203}Pb$. In a particular embodiment the detectable labels are small sized organic PET and SPECT labels such as $^{11}$C, $^{18}$F, $^{124}$I, or $^{125}$I. Other elements and isotopes, such as being used for therapy may also be applied. Metallic radionuclides are suitable incorporated into a chelating agent, for example by direct incorporation by methods known to the skilled artisan.

Suitable fluorophores may be selected from the non-limiting list comprising fluorescein, Alexa Fluor, Oregon Green, acridine, dansyl, NBP, BODIPY, and rhodamine.

Imaging agents for MRI may be paramagnetic ions or superparamagnetic particles. Examples of paramagnetic ions may be selected from the group comprising Gd, Fe, Mn, Cr, Co, Ni, Cu, Pr, Nd, Yb, Tb, Dy, Ho, Er, Sm, Eu, Ti, Pa, La, Sc, V, Mo, Ru, Ce and Dy.

Suitable X-ray responsive agents include but are not limited to Iodine, Barium, Barium sulphate, Gastrofrafin, or can comprise a vesicle, liposome or polymer capsule filled with Iodine compounds and/or barium sulphate.

An 'amino acid' as used herein refers to any one of the 20 common proteinogenic amino acids, i.e. any one of arginine (Arg), histidine (His), lysine (Lys), aspartic acid (Asp), glutamic acid (Glu), serine (Ser), threonine (Thr), asparagine (Asp), glutamine (Glu), cysteine (Cys), glycine (Gly), proline (Pro), alanine (Ala), isoleucine (Ile), leucine (Leu), methionine (Met), phenylalanine (Phe), tryptophan (Trp), tyrosine (Tyr), or valine (Val). For example, when describing the compounds of the invention wherein $R_7$ is not directly attached to the carbonyl through an amino acid, it is meant to exclude the following compounds of the following formula:

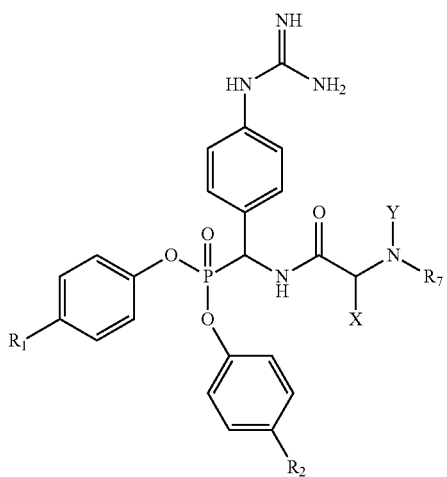

wherein X is an amino acid side chain (e.g. methyl of amino acid alanine), Y is any atom or group, X and Y optionally being bonded together in the case of proline, and $R_7$ is as defined in any one of the different embodiments of the present invention.

In a further embodiment, the present invention provides those compounds wherein there are at least two (in particular at least three, more in particular at least four) atoms between a heteroatom in -$L_1$-Cy-$L_2$- and the nitrogen to which $R_3$ is attached.

In another particular embodiment, the present invention provides those compounds of formula I, wherein $L_1$ is a direct bond or an optionally substituted group selected from —$C_{1-20}$alkyl, —$C_{1-20}$alkenyl, and —$C_{1-20}$alkynyl, wherein said —$C_{1-20}$alkyl-, —$C_{1-20}$alkenyl-, and —$C_{1-20}$alkynyl- is optionally substituted with one or more R' groups, and wherein optionally one or more non-adjacent carbon atoms in said —$C_{1-20}$alkyl-, —$C_{1-20}$alkenyl-, or —$C_{1-20}$alkynyl- are replaced by O, NR", or S; and wherein R' and R" are as defined in claim 1.

In a further embodiment, the present invention provides those compounds wherein $L_1$ is a direct bond, —($C_{1-6}$alkyl-O)$_n$—, or an optionally substituted group selected from —$C_{1-20}$alkyl, —$C_{1-20}$alkenyl, and —$C_{1-20}$alkynyl, wherein said —$C_{1-20}$alkyl-, —$C_{1-20}$alkenyl-, and —$C_{1-20}$alkynyl- is optionally substituted with one or more R' groups;

wherein R' is as defined in claim 1; and wherein n is an integer from 1 to 10.

In a preferred embodiment, the present invention provides those compounds as described herein wherein $R_3$ is —C(=O)O$R_4$ or —S(=O)(=O)$R_6$.

In another particular embodiment, the present invention provides those compounds wherein $R_4$, $R_5$, $R_6$, and $R_7$ are $L_1$-X-$L_2$-Det;

$L_1$ and $L_2$ are each independently a direct bond, —($C_{1-6}$alkyl-O)$_n$—, or an optionally substituted group selected from —$C_{1-20}$alkyl, —$C_{1-20}$alkenyl, and —$C_{1-20}$alkynyl, wherein said —$C_{1-20}$alkyl-, —$C_{1-20}$alkenyl-, and —$C_{1-20}$alkynyl- is optionally substituted with one or more R' groups, and wherein optionally one carbon atoms in said —$C_{1-20}$alkyl-, —$C_{1-20}$alkenyl-, or —$C_{1-20}$alkynyl- is replaced by O, NR", S;

X is selected from a direct bond, cycloalkyl, heterocyclyl, aryl, heteroaryl, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR", wherein said cycloalkyl, heterocyclyl, aryl, and heteroaryl is optionally substituted with one or more R' groups;

wherein n is an integer from 1 to 10; and wherein R' and R" are as defined in claim 1.

In yet another particular embodiment, the present invention provides those compounds as described herein wherein Det is hydrogen. In a further embodiment, those compounds wherein $L_2$ is a direct bond and Det is hydrogen. Compounds wherein Det is hydrogen are especially preferred for use as a medicine. Indeed, in standard therapeutic applications, no detection of the compounds is necessary, thus obviating the need for a detectable label.

In another particular embodiment, the present invention provides those compounds as described herein wherein Det is a detectable label. Said compounds are particularly useful for the detection of KLK4, e.g. in KLK4-expressing tissue. A particular application of these compounds is the detection of KLK4-expressing tumors, either in vivo or in vitro. In a particular embodiment, the present invention provides a method for detecting KLK4, the method comprising administering a compound of the invention wherein Det is a detectable label to a subject and detecting the detectable label of the compound. It should be noted that such a detection method is non-therapeutic. In particular, the method comprises a single administration of a low dose (e.g. below 0.5 mg/kg, in particular below 0.3 mg/kg) of the compounds comprising a detectable label. Said one-time administration of a low dose does not have a therapeutic effect, but is sufficient for the in vivo detection of the compounds, and thus, KLK4.

In another particular embodiment, the present invention provides an in vitro method for the detection of the presence or absence of KLK4, the method comprising:
  providing a sample potentially comprising KLK4;
  contacting said sample with the compound of the invention wherein Det is a detectable label; and
  detecting the detectable label of the compound, thereby detecting the presence or absence of KLK4 in said sample.

Both the in vivo and in vitro method are particularly useful for the diagnosis of a KLK4-related disease, such as but not limited to cancer and an inflammatory disease; more in particular said cancer is selected from ovarian cancer and prostate cancer.

As described herein before, the chemical template described in the Markush formula are useful as a medicine. As far as we know the compounds reported here are the first potent irreversibly binding non peptidic KLK4 inhibitors. The compounds covered by the claims can be used as new therapies for cancer with as example but not limited to prostate, breast and ovarian cancer (Schmitt, Magdolen et al. 2013). In particular the here described combination between the diphenyl phosphonate, the phenyl guanidine and specific tail represents the minimal required structural combination to deliver selective and potent irreversibly binding KLK4 inhibitors. While similar, but structurally different compounds have been described before, none of the articles mention KLK4 inhibition or even suggested that phosphonates can be developed to inhibit KLK4. For example, Joossens et al. (2007) and the associated patent application WO2007045496 describe compounds having a benzyl guanidyl group in the warhead as uPA inhibitors. In addition to the silence of these documents on KLK4 activity, replacement of the benzyl guanidyl group by a phenyl guanidyl group, as present in the compounds of the invention, drastically abolishes uPA inhibitory activity (as shown in the experiments).

Furthermore, most experts in the field teach that selectivity in activity-based probes targeting proteases, is usually obtained by introducing a peptidic part that is ideally specifically recognized by binding sites within or in the near proximity of the active site of the protease. Consequently, when designing KLK4 inhibitors, the skilled person would try to identify the peptidic recognition sequence and try to incorporate or substitute those in known peptidase inhibitors. However, these peptidic compounds suffer from the disadvantages of peptides, i.e. low membrane permeability and metabolic instability. In the current invention we have surprisingly identified that the right combination of a phenyl guanidine moiety and a diphenyl warhead generated potent KLK4 inhibitors, without the necessity for peptidic tails. Therefore, in particular, $R_7$ is not linked to the carbonyl to which it is attached through amino acid.

In addition, selectivity and potency towards KLK4 can even be increased by incorporating a heteroatom at a specific location in the tail. Surprisingly, the incorporation of a heteroatom with at least 4 atoms located between the heteroatom and the nitrogen to which $R_3$ is attached delivered potent and selective covalently (irreversibly) binding KLK4 inhibitors with optimal properties for drug development. Particularly preferred compounds are those wherein there from 4 to 9 atoms between a heteroatom in $R_3$ and the nitrogen to which $R_3$ is attached. These tails avoid the use of a peptic chain as driver for selectivity. In drug design small molecules are still considered as advantageous over peptidic compounds.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

The present invention also provides a composition comprising a compound according to the invention. In particular a pharmaceutical composition, comprising one or more pharmaceutically acceptable carriers. In a particular embodiment, the present invention provides a compound or composition of the invention for use in the treatment or prevention of a KLK4-associated disease or disorder, such as cardiovascular diseases, cancer, endocrinological diseases, metabolic diseases, gastroenterological diseases, inflammation, hematological diseases, respiratory diseases, neurological diseases, reproduction disorders and urological diseases. In particular, said KLK4-related diseases is selected from cancer and an inflammatory disease, more in particular cancer, such as selected from ovarian cancer and prostate cancer. In addition, the present invention provides a compound according to the invention for the preparation of a medicament for the treatment or prevention of a KLK4-associated disease. In another particular embodiment, the present invention provides a method for the treatment or prevention of a KLK4-related disease or disorder, the method comprising administering a therapeutically effective amount of a compound of the invention to a subject in need thereof. Treatment as used herein comprises both prophylactic and therapeutic treatment. In a particular embodiment, the present invention provides a method for therapeutic treatment, comprising administering a compound of the invention to a subject having a KLK4-related disease.

Activity based probes, are specially designed chemical probes that react with specific classes of enzymes. The probes typically consist of two elements: a reactive group and a tag (also termed detectable label). Additionally, some probes may contain an additional group which enhances selectivity. The reactive group usually contains an electrophile that gets covalently-linked to a nucleophilic residue in the active site of an active enzyme. The detectable label may be, but is not limited to a reporter or visualization tag such as a fluorophore, an enrichment handle such as biotin, or an additional derivatization point for secondary introduction of reporter, visualization or enrichment tags. In chemical terms, such derivatization points can rely on any suitable reaction type to obtain tagged probes. Examples include, but are not limited to azides and alkynes for derivatization via Huisgen 1,3-dipolar cycloaddition (also known as click chemistry). A major advantage of the activity based probes technology is the ability to monitor the availability of the enzyme active site directly, rather than being limited to protein or mRNA abundance. With classes of enzymes such as the serine proteases that often interact with endogenous inhibitors or that exist as inactive zymogens, this technique offers a valuable advantage over traditional techniques that rely on abundance rather than activity.

Existing technologies to monitor proteins rely on nonspecific activity-based probes, peptidic probes, internally quenched fluorescent substrates and antibodies. They all suffer from one or more of the following disadvantages: lack of potency and selectivity, n covalent bond formation or no correlation with protein activity, low cell permeability and stability, no straightforward derivatisation with reporter or imaging tags.

The addition of one or more heteroatoms, example given but not limited to H-acceptor atoms between 6 and 11 atoms counting from the alpha atom (i.e. the carbon atom to which phenyl guanidine is attached), leads to even more selective and potent KLK4 activity based probes.

In a particular embodiment, the present invention provides those compounds that show KLK4 inhibitory activity with a kapp higher than $10^2$ $M^{-1}$ $s^{-1}$ A chemical moiety of formula I, consisting of a diphenyl phosphonate warhead, phenyl guanidine group and a tail part with a heteroatom can be used as inhibitors or activity based probes targeting selectively KLK4. Especially preferred are those compounds wherein a heteroatom is located in the tail with at least 4 atoms between said heteroatom and the amine to which $R_3$ is attached. They show fast kinetic binding parameters and potent $IC_{50}$ values after a short 15 min incubation period. The speed of the reaction will be beneficial for their use in preclinical and clinical settings. The KLK4-selectivity was determined with respect to 12 closely related serine proteases. The here described inhibitors and probes are up till now the most potent and selective compounds directed to KLK4 that do not interfere with proteases of the blood coagulation and fibrinolysis cascades. It is very important to understand the difference between an $IC_{50}$ value of an irreversible inhibitor and an $IC_{50}$ value of a reversible inhibitor. The $IC_{50}$ value of a reversible inhibitor is related to an equilibrium constant (Ki) and the $IC_{50}$ value of an irreversible inhibitor is related to kinetic parameters such as the overall second order rate constant of inhibitor binding or the first order inactivation rate constant. We called the overall second order rate constant of binding $k_{app}$ because it is dependent upon conditions of the assay, for instance the substrate concentration. When the substrate concentration used is equal to the Km, the overall rate constant of binding will be $2*k_{app}$. Irreversible binding can have the benefit over reversible binding that the target activity is inhibited for a very long time and that the natural substrate cannot compete with the inhibitor. The natural substrates will compete with the inhibitor for binding but once the covalent complex is formed, the natural substrates can no longer displace the inhibitor from its binding site, even when the free inhibitor is cleared from the circulation and tissues. Particular in life threatening diseases such as cancer and infectious diseases irreversible inhibition can be preferred over reversible inhibition. Even more, a diphenyl phosphonate group is a reactive moiety and is preferably used when covalent binding is anticipated. If a diphenyl phosphonate compound reacts via a reversible mechanism, the group may be considered a disadvantage for further drug development because the asset of long and complete inhibition is not obtained, although the group might retain reactivity towards other potential targets. Diphenyl phosphonates of the invention with a $k_{app}$ higher than $10^4$ $M^{-1}s^{-1}$ are preferred, as they will be the first choice to move forward as preclinical drug candidates. Diphenyl Phosphonates with lower $k_{app}$ values may be considered to have a too slow reaction time compared to their in vivo stability. With other words, there is a chance that the diphenyl warhead will be destroyed before it can react with the target in certain in vivo settings. The $IC_{50}$ value is depending on the assay conditions (e.g. incubation time). In our assay an $IC_{50}$ value lower than 100 nM correlates with a $k_{app}$ higher than $10^4$ $M^{-1}s^{-1}$. For imaging and proteomics probes the ideal kapp is higher than $10^2$ $M^{-1}$ $s^{-1}$ because only a fraction of the target need to be labeled to allow visualization.

EXAMPLES

General Synthesis Schemes

Scheme 1 and Scheme 3 outline the general synthetic strategy to obtain the diaryl phosphonates of the present invention. The key reaction for synthesizing the probes is the Birum-Oleksyszyn reaction. This reaction requires an aldehyde, a carbamate, a phosphite and a catalyst. If a lewis acid as catalyst is used, the molecule can contain an acid labile Boc-protecting group. Using different carbamates in this reaction gives us the opportunity to introduce different side chains, while the phenyl guanidine-group is maintained. When the carbamate based intermediates contain alkyne as a functional group, the obtained probes (clickable probes) can be conjugated to different visualization tags (e.g. rhodamine, Cy5, DOTA, biotin). This leads to functionalized probes, which can be used for labeling and visualizing KLK4. This is shown in Scheme 4.

Scheme 1: General synthetic scheme for the diaryl phopsphonates with a carbamate side chain

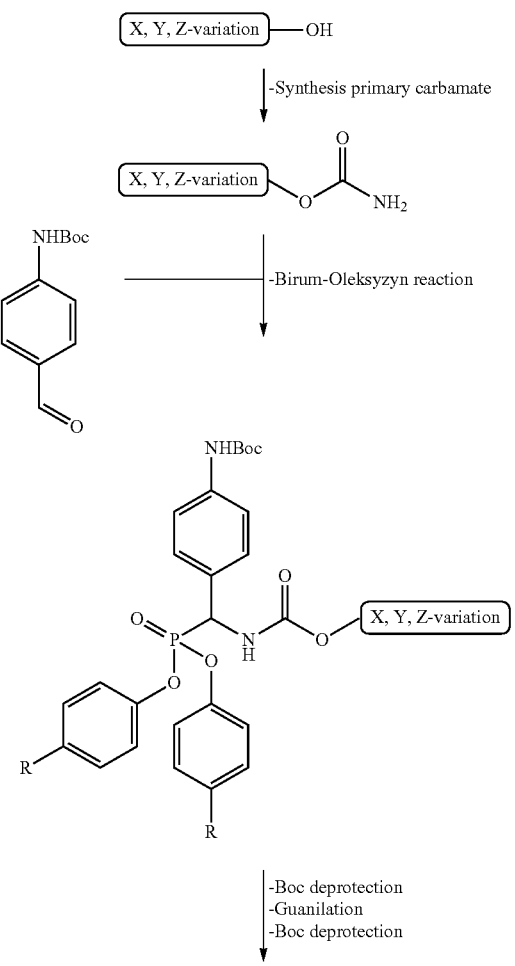

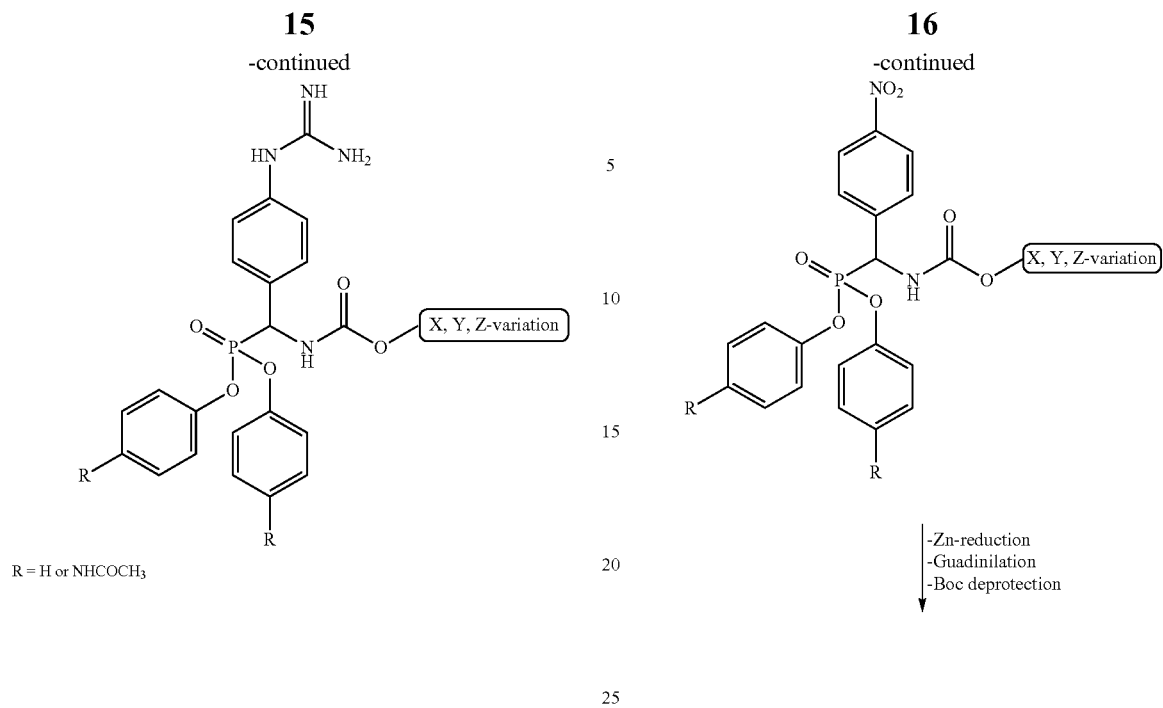
R = H or NHCOCH₃
Scheme 2: Synthesis of the diarylphosphonates using paranitro benzaldehyde
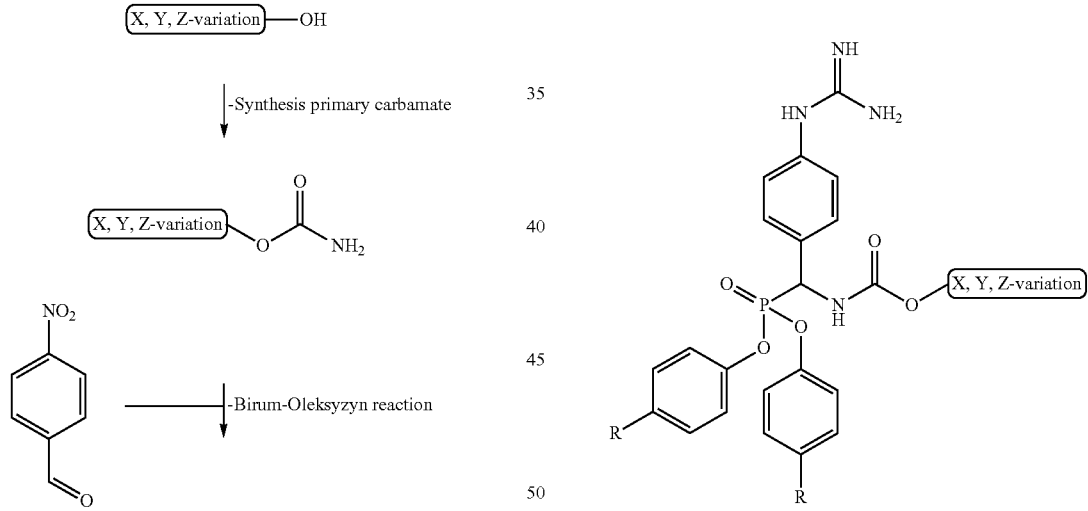
Scheme 3: General synthetic scheme for the diaryl phopsphonates with a (sulfon)amide side chain
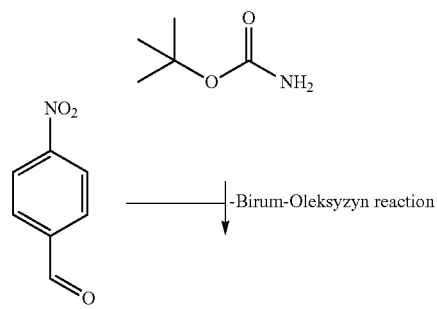

-continued
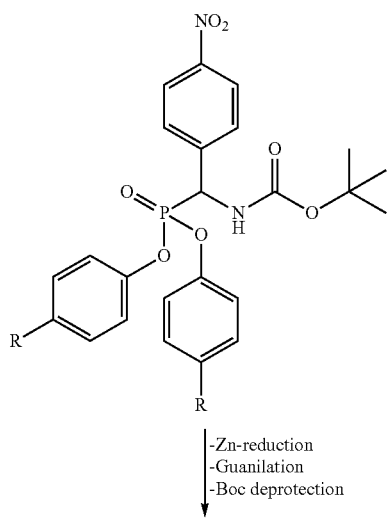
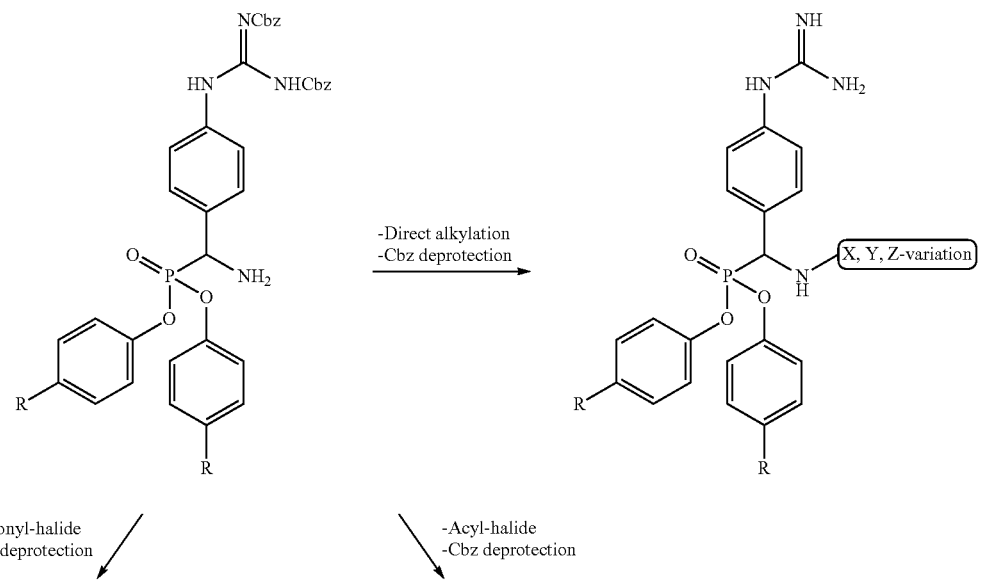
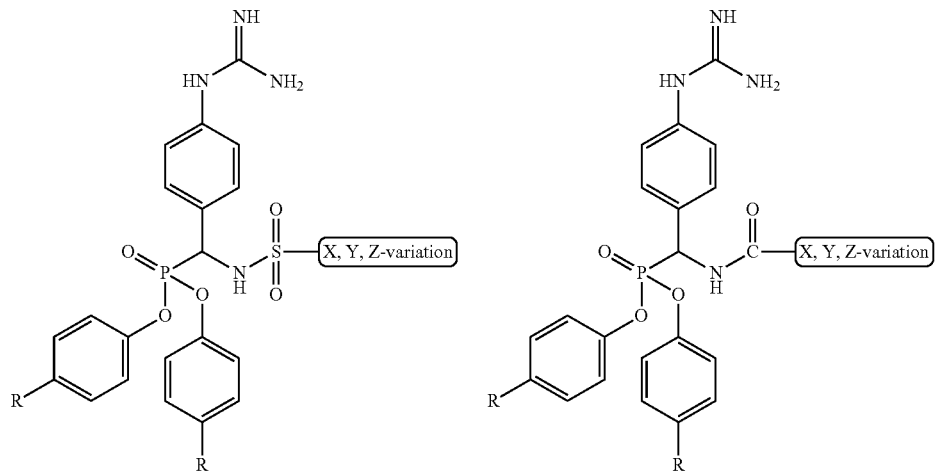
R = H or NHCOCH₃

Scheme 4: General synthetic scheme for the functionalized probes

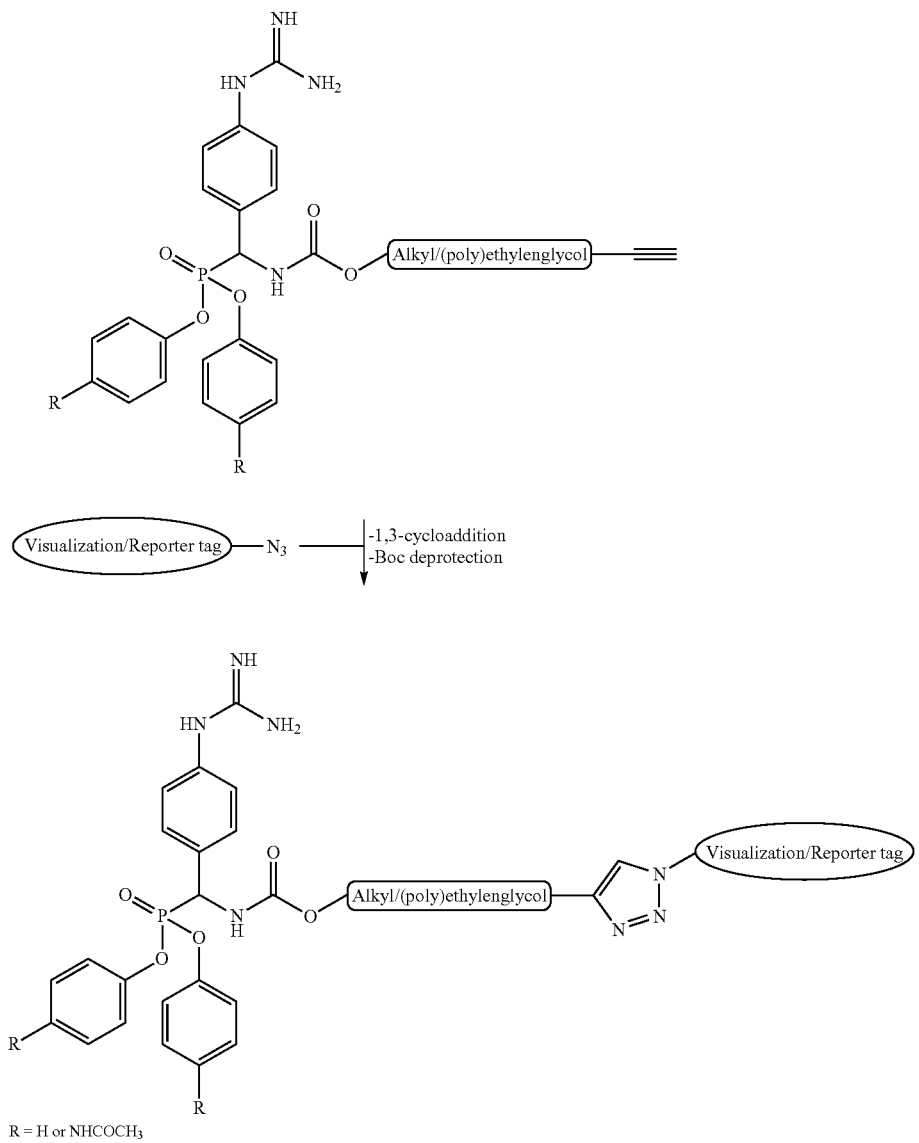

R = H or NHCOCH₃

Scheme 5 shows the synthesis of the different carbamates. Trichloroacetyl isocyanate is used as reagent to convert the alcohols into the corresponding carbamates (intermediates 3-7 and 84-88). To obtain 8 an extra addition reaction was performed. The alcohols were bought as such, or were made from commercially available ethylene glycol via a nucleophilic substitution reaction. Methyl-, ethyl- and benzyl-carbamate were commercially available.

Boc-protected 4-aminobenzaldehyde (11) was synthesised from the corresponding Boc-protected alcohol (10) with Dess-Martin periodinane. Boc-protected 4-aminobenzaldehyde was used together with the various carbamates (3-6, 8) to yield diaryl phosphonates 1A, 12-16 in an adapted Birum-Oleksyszyn reaction (Joossens, Ali et al. 2007). After acidolytic removal of the Boc-protecting group N,N'-bis(tert-butoxycarbonyl)-1-guanylpyrazole was used to introduce the protected guanidine group (3A, 22-26, 91). Boc deprotection afforded the products 4A, 27-31, 92 (Scheme 6). Alternatively paranitro benzaldehyde was used together with the carbamates (85-88, 4) and aryl sulfonamides (115-118) to yield diaryl phosphonates 95-98, 111, 115-118 in the adapted Birum-Oleksyszyn reaction. After reduction of the nitro group with zinc, N,N'-bis(tert-butoxycarbonyl)-1-guanylpyrazole was used to introduce the Boc-protected guanidine group (103-106, 113, 123-126). Boc deprotection afforded the products 107-110, 114, 127-130.

Diaryl phosphonate 132 was synthesized by removing the Cbz and Boc groups with HBr in acetic acid.

Piperazine rhodamine (62) was synthesized via a known literature procedure. (Nguyen and Francis 2003). Coupling with 8-azidooctanoic acid (intermediate 61) yielded azido-rhodamine (63) (Scheme 11).

The methyl Cy₅-dye 68 was synthesized using an existing literature procedure (Jung and Kim 2006). An azide functionality was inserted via the coupling of 2-azido ethaneamine 70 to the acid of 68 to yield the Cy5-azide 71. (Scheme 12)

Biotin-azide 75 was synthesized starting from the commercially available biotin (72). The carboxylic acid functionality was first transformed into NHS-ester (74) by a coupling reaction with DCC and NHS. This was coupled with 2-(2-(2-(2-azidoethoxy)ethoxy)ethoxy)ethanamine to yield biotin-azide 75 (Scheme 13). These azide-linked labels were connected to 19 via a Cu-catalysed 1,3-cycloaddition reaction to yield the individual probes 78-81 after a Boc-deprotection (Scheme 15). The DOTA-labeled probe 83 was made by reacting a DOTA-NHS ester with the free amine of 81 (Scheme 16).

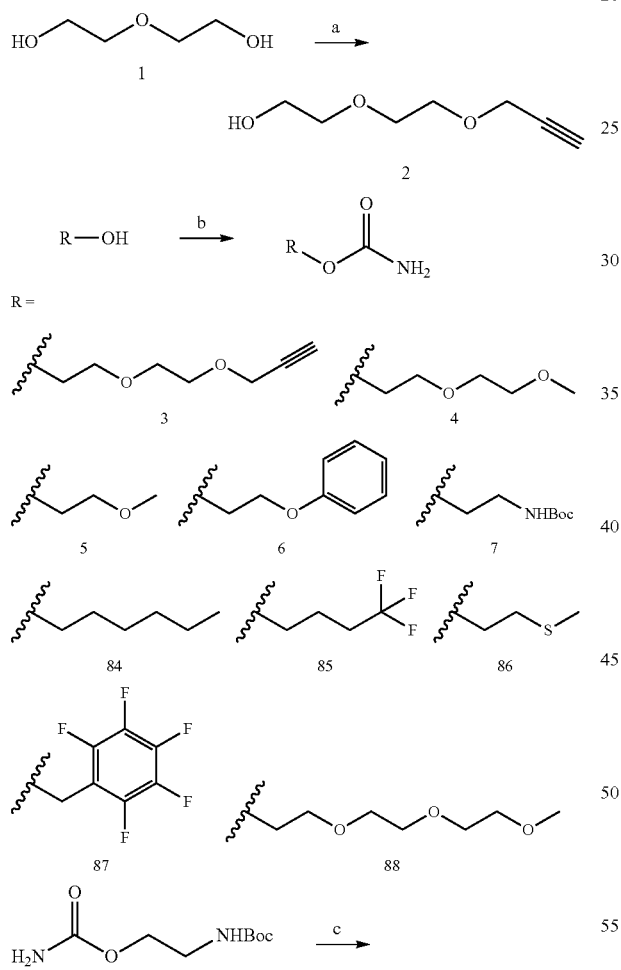

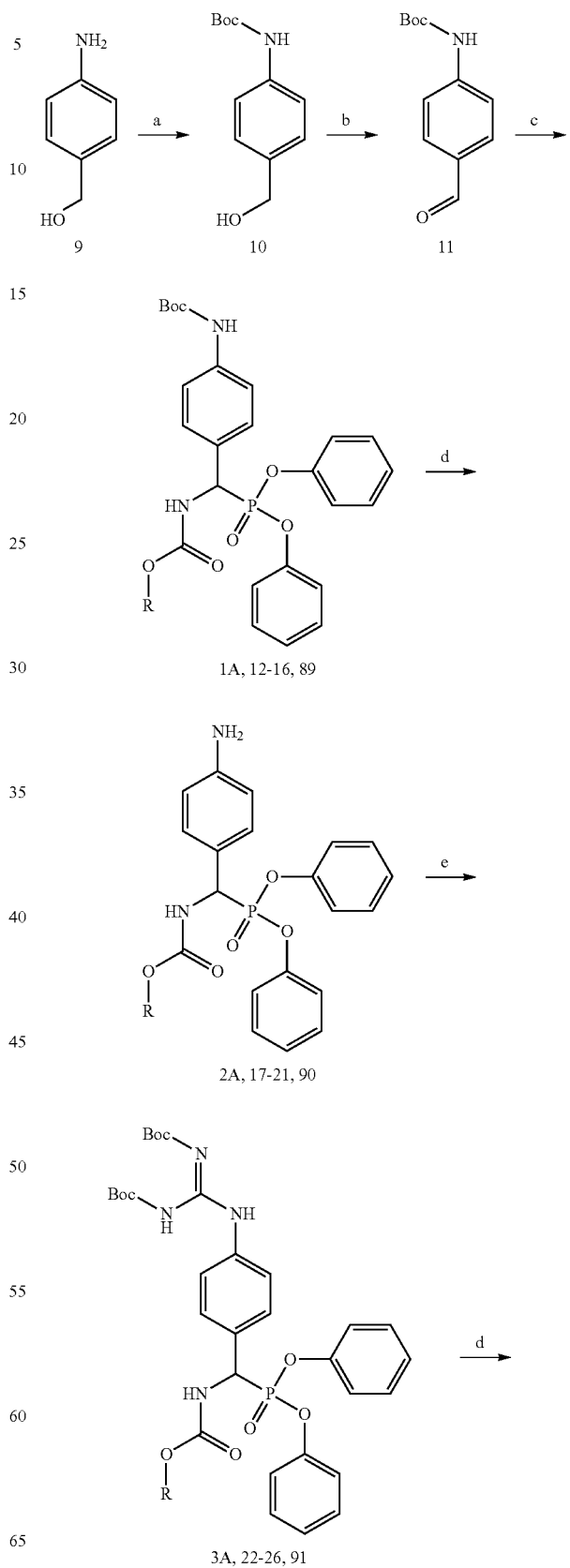

23
-continued
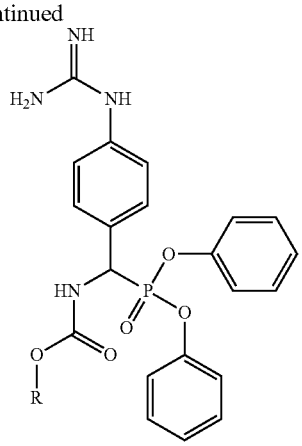
5A, 27-31, 92
R =
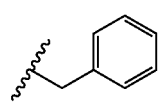
1A, 2A, 3A, 5A
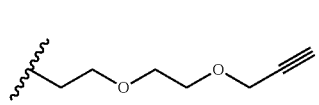
12, 17, 22, 27
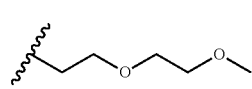
13, 18, 23, 28
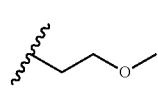
14, 19, 24, 29
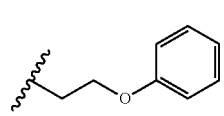
15, 20, 25, 30
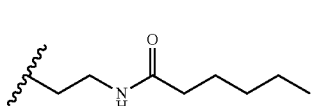
16, 21, 26, 31
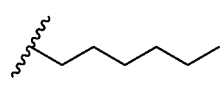
89, 90, 91, 92
Reagents and conditions: (a) (Boc)$_2$O, TEA, Dioxane (b) Dess-Martin Periodane, DCM (c) for 27-31 and 35-54: Cu(OTf)$_2$, P(OPh)$_3$, DCM or for 32-34: Cu(OTf)$_2$, triparacetamol-phosphite, DCM (d) TFA, DCM (e) TEA, DCM, N,N'-bis(tert-butoxycarbonyl)-1-guanylpyrazole
Scheme 7: Synthesis of diaryl phosponates 107-110, 114
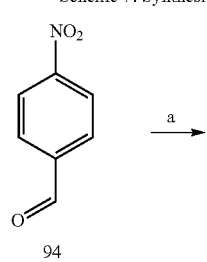
94
24
-continued
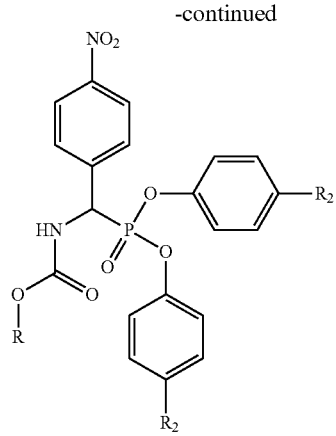
95-98, 111
b →
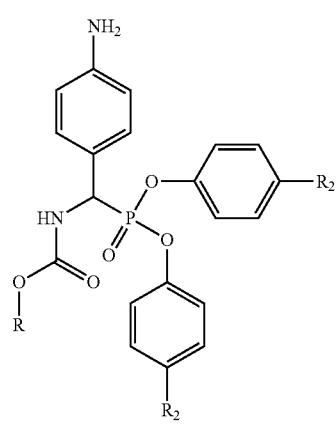
99-102, 112
c →
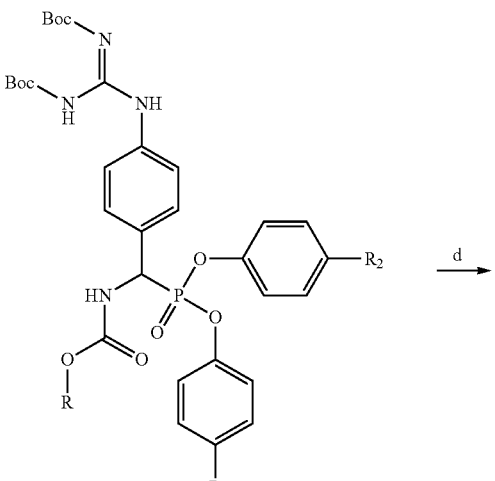
103-106, 113
d →

-continued
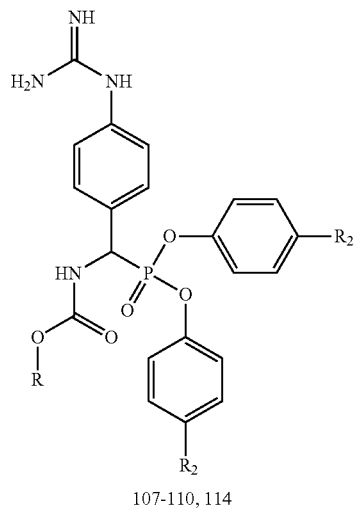
107-110, 114
-continued
R2 = H, R1 =
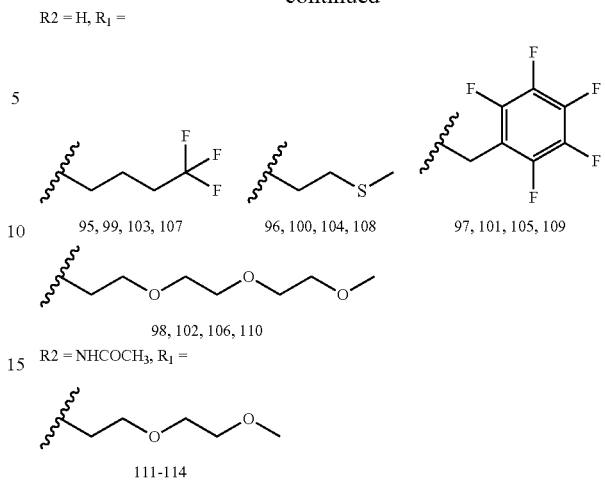
95, 99, 103, 107      96, 100, 104, 108      97, 101, 105, 109
98, 102, 106, 110
R2 = NHCOCH3, R1 =
111-114
Reagents and conditions: (a) 95-99: Cu(OTf)$_2$, P(OPh)$_3$, DCM or for 111: Cu(OTf)$_2$, triparacetamol-phosphite, DCM (b) Zn, THF/NH$_4$Cl$_{sat}$ (c) DCM, N,N'-bis(tert-butoxycarbonyl)-1-guanylpyrazole (d) TFA, DCM
TABLE 1
Diaryl phosphonates 27-31, 92, 107-110, 114 prepared as shown in Scheme 6 & Scheme 7
| Nr | R | R' |
|---|---|---|
| 27 | propargyl-PEG2 | H |
| 28 | methoxy-PEG2 | H |
| 29 | methoxypropyl | H |
| 30 | phenoxyethyl | H |

TABLE 1-continued
Diaryl phosphonates 27-31, 92, 107-110, 114 prepared as shown in Scheme 6 & Scheme 7
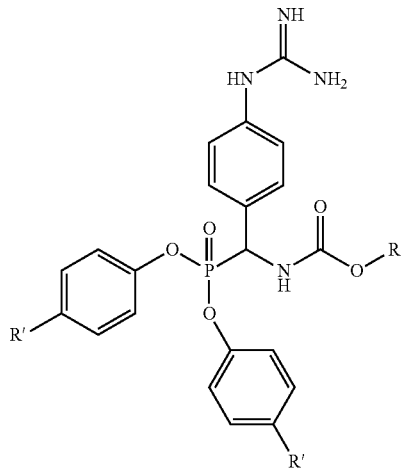
| Nr | R | R' |
|---|---|---|
| 31 | propyl-NH-C(O)-pentyl | H |
| 92 | heptyl | H |
| 107 | butyl-CF$_3$ | H |
| 108 | ethyl-S-methyl | H |
| 109 | ethyl-pentafluorophenyl | H |
| 110 | propyl-O-CH$_2$CH$_2$-O-CH$_2$CH$_2$-O-methyl | H |
| 114 | ethyl-O-CH$_2$CH$_2$-O-methyl | NHCOCH$_3$ |

Scheme 8: Synthesis diaryl phosphonates with (sulfon)amides as side chain
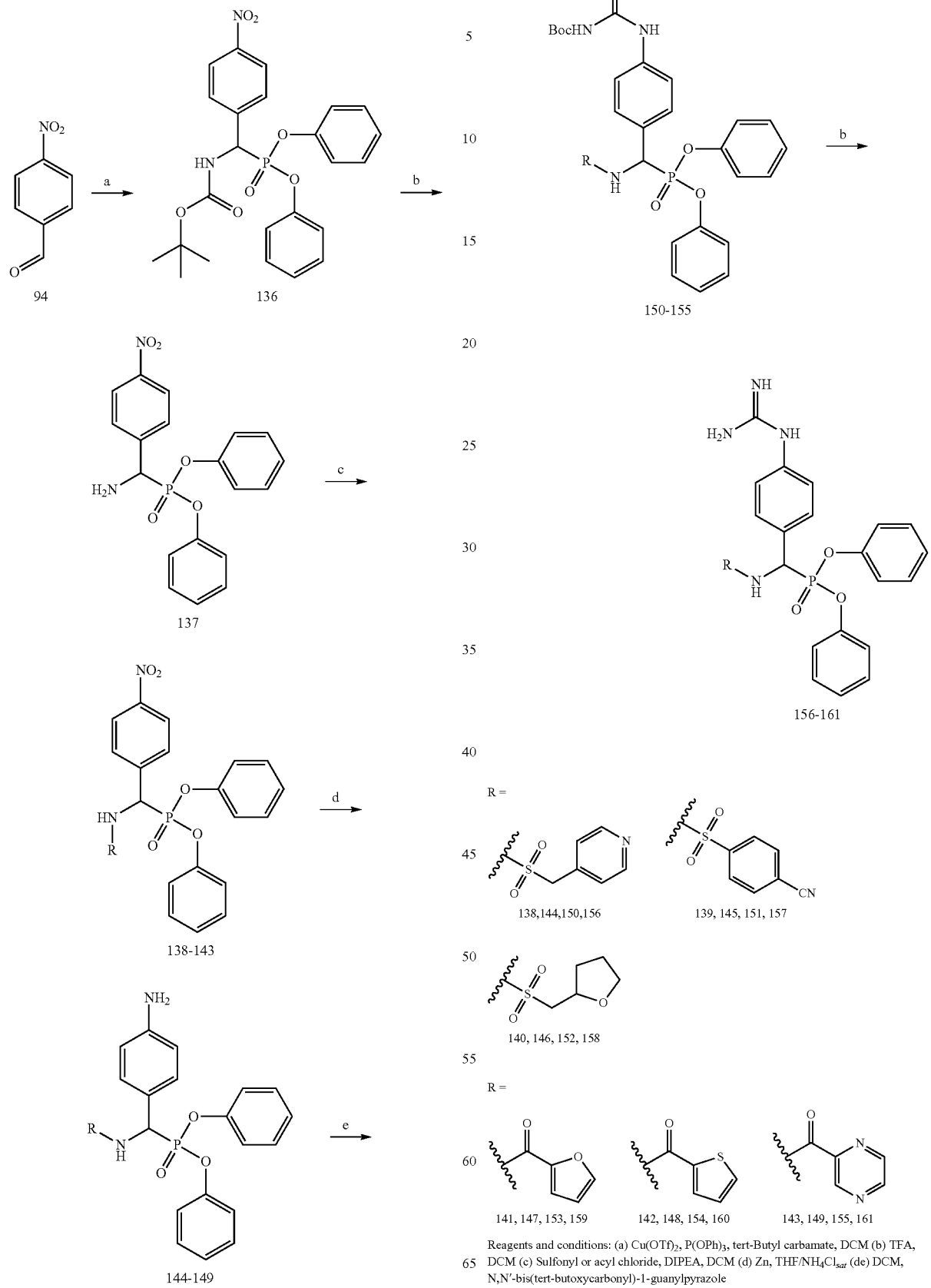
Reagents and conditions: (a) Cu(OTf)$_2$, P(OPh)$_3$, tert-Butyl carbamate, DCM (b) TFA, DCM (c) Sulfonyl or acyl chloride, DIPEA, DCM (d) Zn, THF/NH$_4$Cl$_{sat}$ (de) DCM, N,N'-bis(tert-butoxycarbonyl)-1-guanylpyrazole

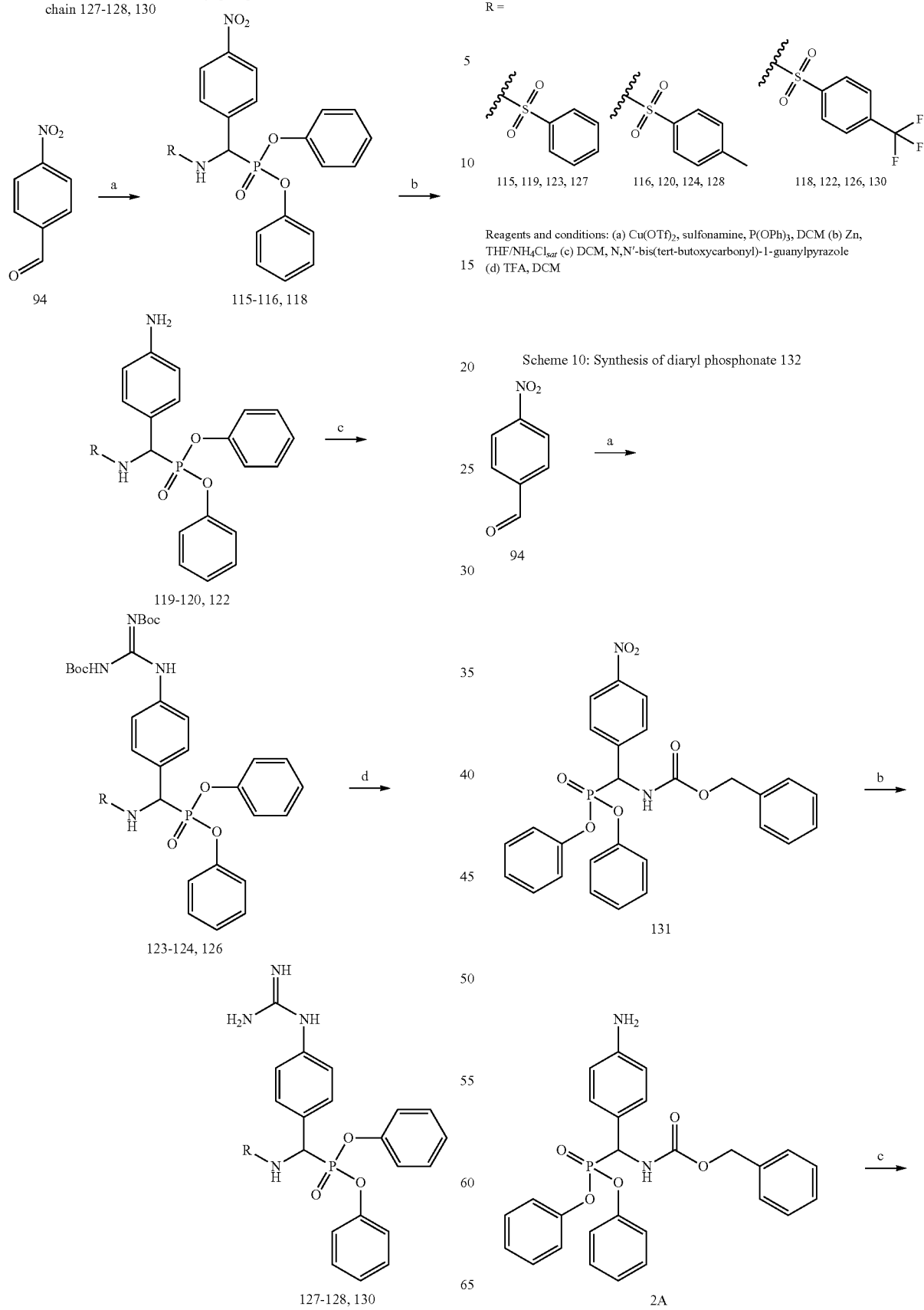

33
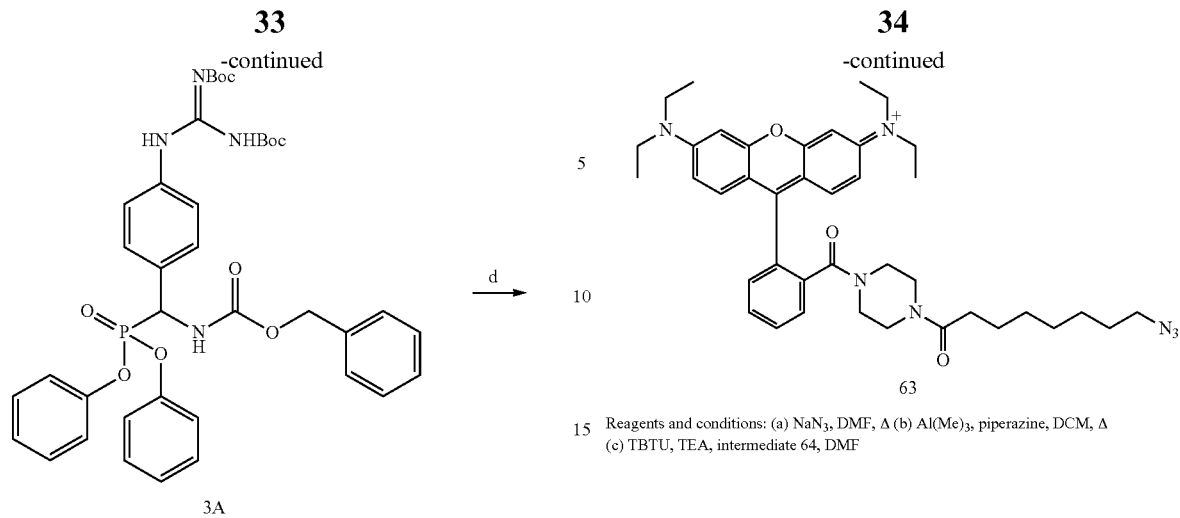
3A
Reagents and conditions: (a) Cu(OTf)$_2$, sulfonamine, P(OPh)$_3$, DCM (b) Zn, THF/NH$_4$Cl$_{sat}$ (c) DCM, N,N'-bis(tert-butoxycarbonyl)-1-guanylpyrazole (d) HBr(33%) in acetic acid
Scheme 11: Synthesis of Rhodamine-azide
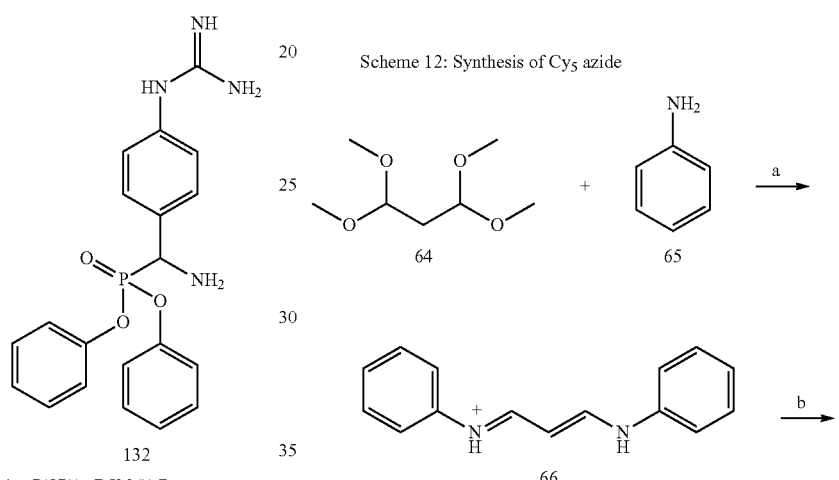
34
63
Reagents and conditions: (a) NaN$_3$, DMF, Δ (b) Al(Me)$_3$, piperazine, DCM, Δ (c) TBTU, TEA, intermediate 64, DMF
Scheme 12: Synthesis of Cy$_5$ azide
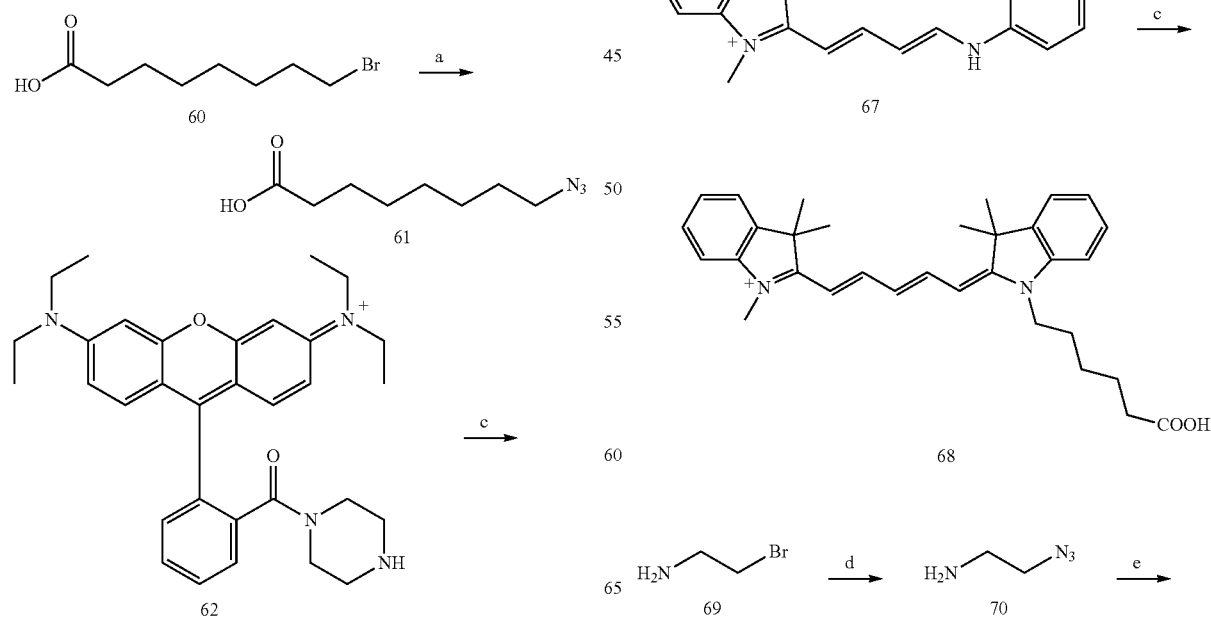

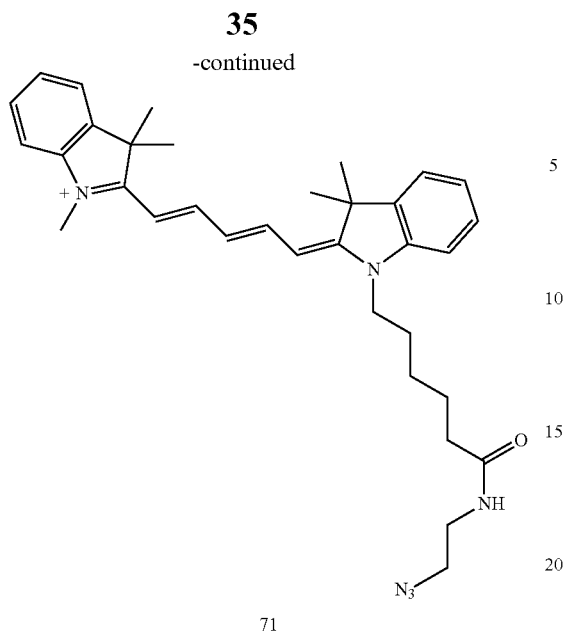
71
Reagents and conditions: (a) HCl$_{aq}$, 50° C., (b) Fischer's base, AcOH, reflux, (c) EtOH, sodium acetate, reflux, (d) Sodium azide, Water, 80° C., (e) TBTU, DIPEA, 68, DMF
Scheme 14: Synthesis of tail for a DOTA-labeled-probe
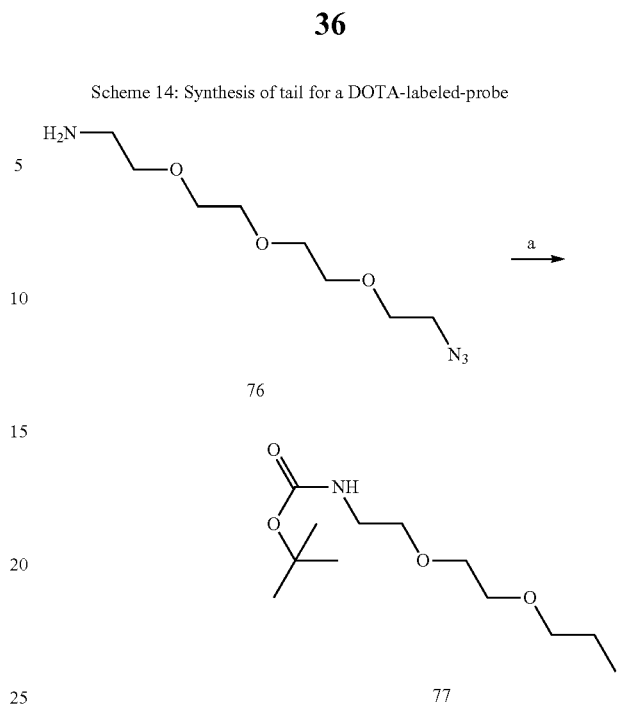
Reagents and conditions: (a) Boc$_2$O, DCM
Scheme 13: Synthesis of biotin-azide
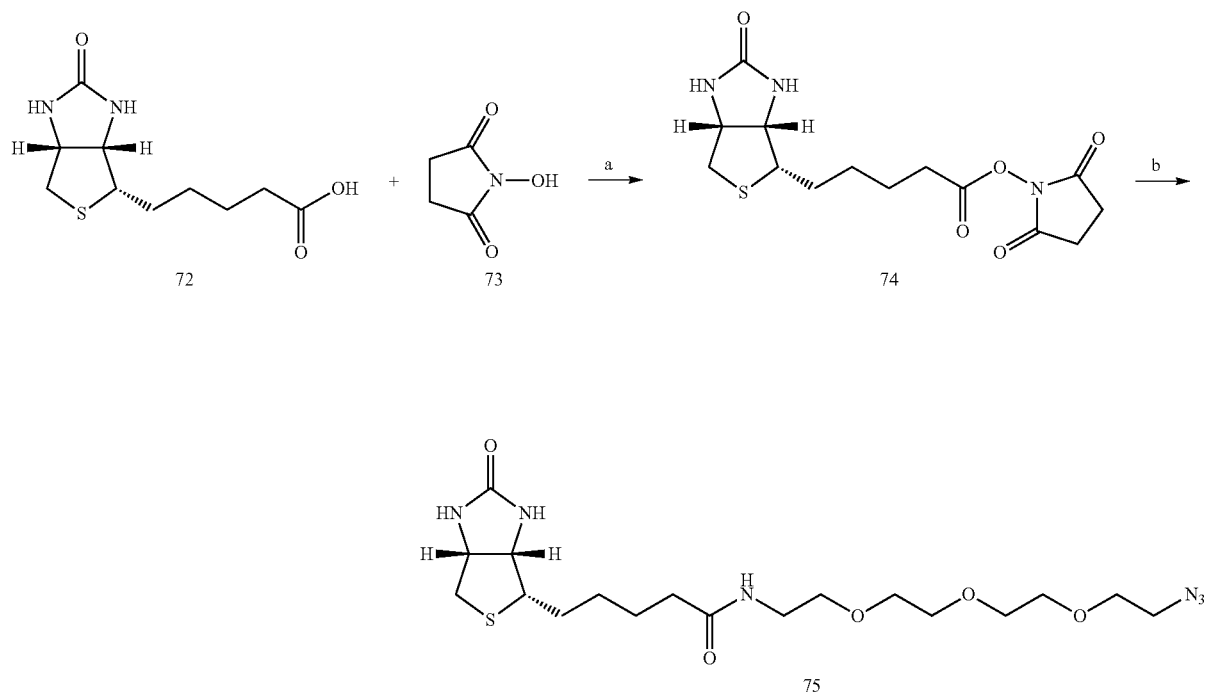
Reagents and conditions: (a) DCC, DMF (b) 2-(2-(2-(2-azidoethoxy)ethoxy)ethoxy)ethanamine, triethylamine, DMF Scheme 15: Synthesis of the functionalized probes
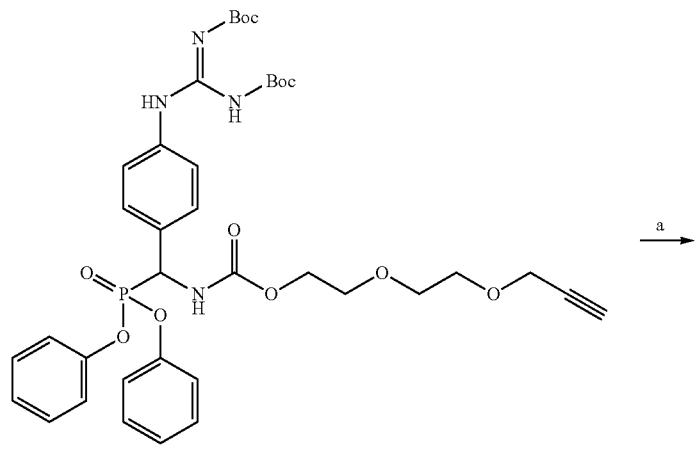
22
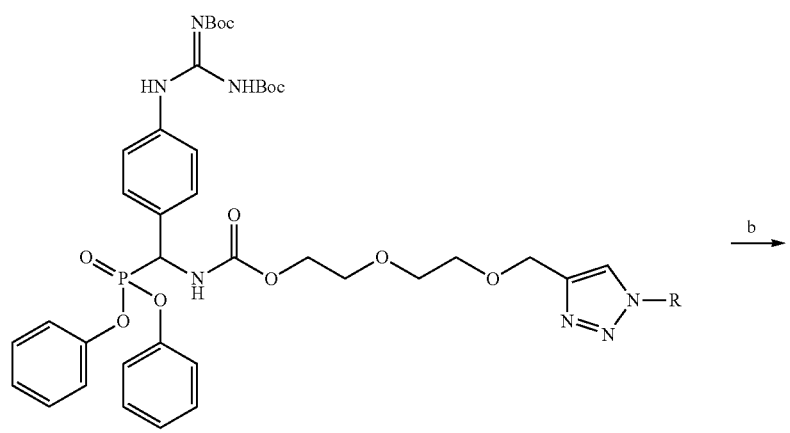
78-81
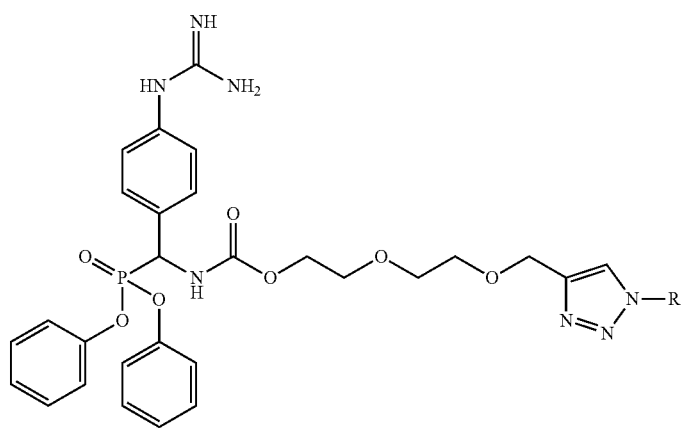
82, 133-135

R =
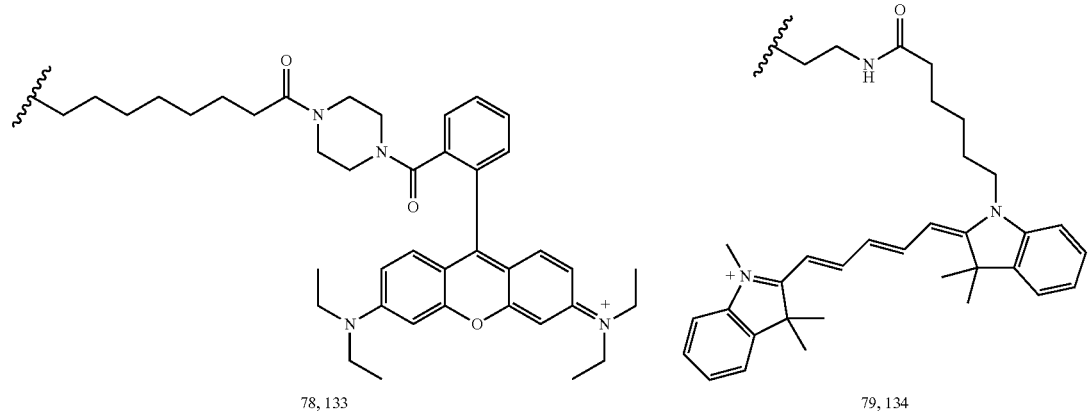
78, 133
79, 134
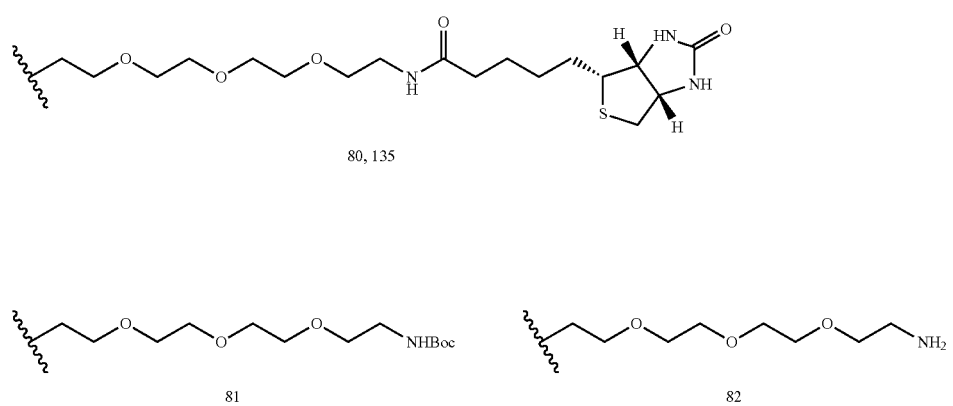
80, 135
81
82
Reagents and conditions: (a) i) Cu(II)SO₄, Na-ascorbate, THF/H₂O, b) TFA, DCM
Scheme 16: Synthesis of a DOTA-labelled-probe
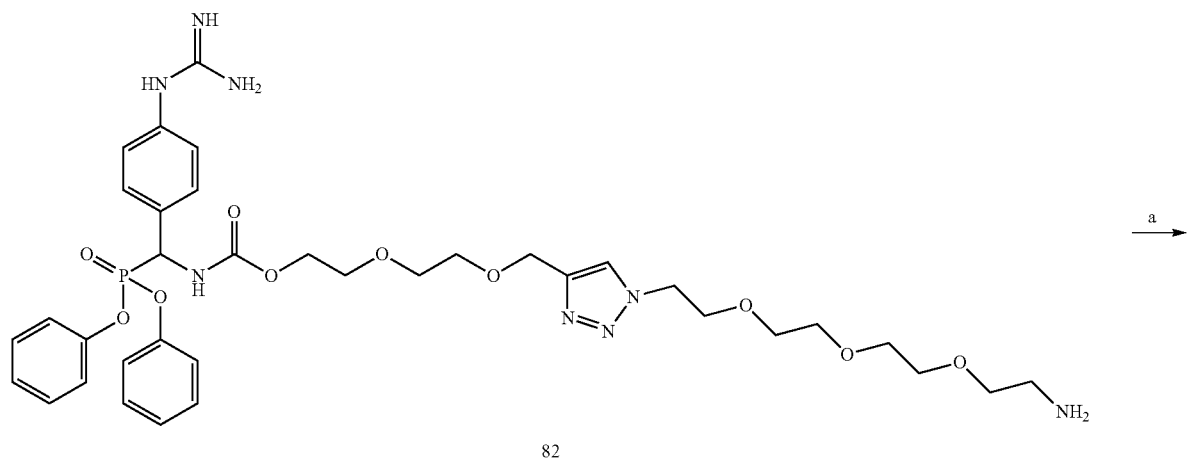
82

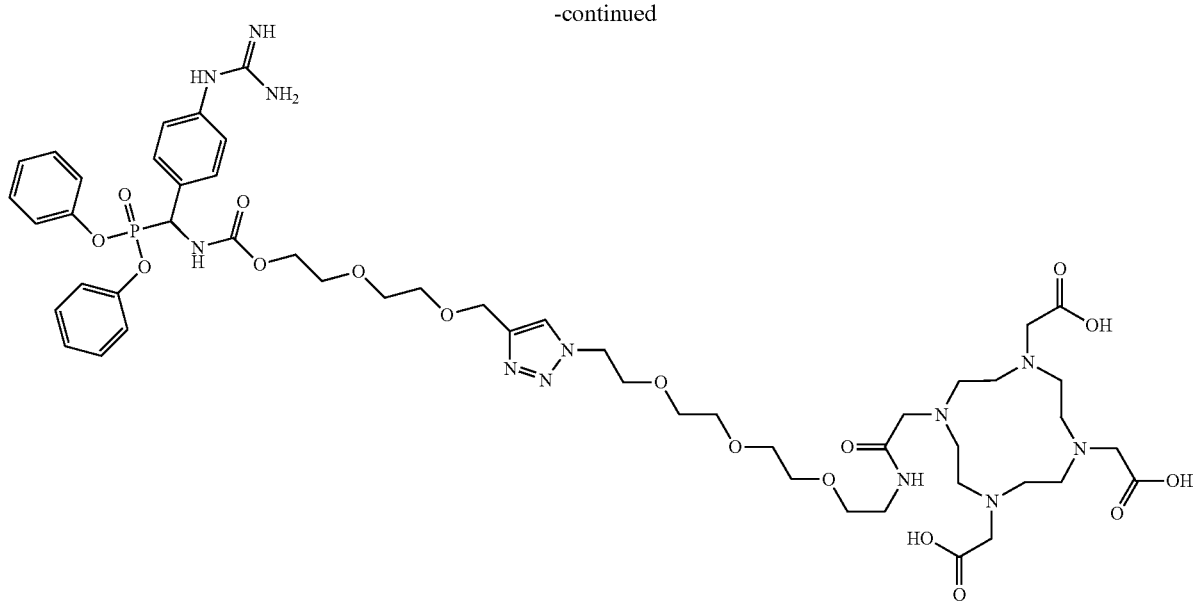

83

Reagents and conditions: (a) DOTA-NHS ester, DIPEA, ACN/DMF

Experimental Procedures

Reagents and solvents were obtained from Sigma-Aldrich, Acros, TCI, Macrocylcis Inc. or Fluorochem. Characterization of all compounds was done with $^1$H NMR and mass spectrometry. $^1$H NMR spectra were recorded on a 400 MHz Bruker Avance III nanobay spectrometer. ES mass spectra were obtained from an Esquire 3000 plus iontrap mass spectrometer from Bruker Daltonics. Purity was verified using one of the following methods: HPLC systems using, a mass or UV-detector or UPLC. Water (A) and CH$_3$CN (B) were used as eluents. LC-MS spectra were recorded on an Agilent 1100 Series HPLC system using a Alltech Prevail C18 column (2.1×50 mm, 3 μm) coupled with an Esquire 3000 plus as MS detector and a 5-100% B, 20 min gradient was used with a flow rate from 0.2 mL/min. Formic acid 0.1% was added to solvents A and B. Reversed phase HPLC was run on a Gilson instrument equipped with an Ultrasphere ODS column (4.6×250 mm, 5 μm). A 10-100% B, 35 min gradient was used with a flow rate from 1 mL/min. Trifluoroacetic acid 0.1% was added to solvent A and B. A wavelength of 214 nm was used. UPLC-MS-data were recorded on a Waters acquity UPLC system coupled to a Waters TQD ESI mass spectrometer and Waters TUV detector. A Waters acquity UPLC BEH C18 1.7 μM 2.1×50 mm column was used. A typical gradient used was: 0.15 min 95% A, 5% B then in 1.85 min to 95% B and 5% A and finally 0.25 min 95% B and 5% A (flow rate 0.350 ml/min.). With solvent A: H$_2$O with 0.1% trifluoroacetic acid and solvent B: Acetonitrile Flash chromatography was performed on a Biotage ISOLERA One system with an internal variable dual-wavelength diode array detector (200-400 nm). SNAP cartridges (10-100 g; flow rate 10 ml/min.-100 ml/min.) were used.

Synthetic Procedure a

Intermediate 2: 2-(2-(prop-2-yn-1-yloxy)ethoxy)ethan-1-ol 2,2'-oxydiethanol (168 mmol) in THF (100 ml) was added dropwise to a solution of sodium hydride (42 mmol) in THF (80 ml) at 0° C. during 30 minutes. The solution was stirred for 2 hours at room temperature. 3-bromoprop-1-yne (42 mmol) was added and the solution was refluxed overnight, followed by addition of water (80 ml). Solvent was evaporated and extracted with EtOAc (4×100 ml). The combined organic layers were washed with brine, dried over anhydrous Na$_2$SO$_4$, filtered and concentrated in vacuo. The obtained mixture was purified with flash chromatography (100% Heptane to 40% EtOAc in Heptane)

Yield: 58.3%, MS (ESI) m/z 167 [M+Na]$^+$ $^1$H-NMR (CDCl$_3$, 400 MHz) δ 2.44 (t, J=2.4 Hz, 1H), 3.62 (t, J=4.4 Hz, 2H), 3.69-3.77 (m, 6H), 4.22 (d, J=2.4 Hz, 2H)

Synthetic Procedure B

Intermediate 3: 2-(2-(prop-2-ynyloxy)ethoxy)ethylcarbamate

To a solution of 2-(2-(prop-2-yn-1-yloxy)ethoxy)ethan-1-ol (8.99 mmol) in dry DCM (50 ml), was added 2,2,2-trichloroacetyl isocyanate (10.79 mmol) at 0° C. After 1 hour stirring at room temperature, the solvent was evaporated and the reaction mixture was dissolved in 30 ml MeOH en 3 ml Water. K$_2$CO$_3$ (15.46 mmol) was added and the reaction was allowed to stir overnight. MeOH was evaporated and water (50 ml) was added. This water layer was extracted twice with EtOAc. The organic layers were combined, washed with brine, dried over anhydrous Na$_2$SO$_4$, filtered and evaporated. A yellow oily liquid was obtained.

Yield: 74% (1.2 g), MS (ESI) m/z 226 [M+K]$^+$ $^1$H-NMR (CDCl$_3$, 400 MHz) δ 2.40 (t, J=2.4 Hz, 1H), 3.65 (m, 6H), 4.20 (m, 4H), 4.90 (br s, 2H)

The following compounds were prepared in a similar way:

Intermediate 4: 2-(2-methoxyethoxy)ethyl carbamate

Yield: 50%, MS (ESI) m/z 164.4 [M+H]$^+$ $^1$H NMR (CDCl$_3$, 400 MHz) δ 3.38 (s, 3H), 3.55 (t, 2H), 3.63 (t, 2H), 3.67 (t, 2H), 4.22 (t, 2H), 5.23 (s, 2H)

Intermediate 5: 2-methoxyethyl carbamate

Yield: 63% MS (ESI) m/z 120.4 [M+H]$^+$
$^1$H NMR (CDCl$_3$, 400 MHz) δ 3.42 (s, 3H), 3.62 (t, 2H), 4.26 (t, 2H), 4.78 (s, 2H).

Intermediate 6: 2-phenoxyethyl carbamate

Yield: 32% MS (ESI) m/z 182.5 [M+H]$^+$
$^1$H NMR (CDCl$_3$, 400 MHz) δ 4.20 (t, 2H), 4.46 (t, 2H), 4.68 (s, 2H), 6.96 (d, 2H), 6.99 (t, 1H), 7.32 (t, 2H).

Intermediate 7 tertbutyl(2-(carbamoyloxy)ethyl)carbamate

Yield: 23%
MS (ESI): m/z 205.4 [M+H]$^+$; Rt: 1.28 min (UPLC)

Intermediate 84 hexyl carbamate

Yield: 95%
1H NMR (CDCl$_3$, 400 MHz) δ 0.83-0.94 (m, 3H), 1.21-1.41 (m, 6H), 1.55-1.67 (m, 2H), 4.04 (t, J=6.8 Hz, 2H), 4.99-5.05 (m, 3H).

Intermediate 85 4,4,4-trifluorobutyl carbamate

Yield: 92%
1H NMR (CDCl$_3$, 400 MHz) δ 1.85-1.97 (m, 2H), 2.11-2.28 (m, 2H), 4.13 (t, J=6.3 Hz, 2H), 4.92-4.98 (m, 2H).

Intermediate 86 2-(methylthio)ethyl carbamate

Yield: 91%
1H NMR (CDCl$_3$, 400 MHz) δ 2.14 (s, 3H), 2.72 (t, J=6.8 Hz, 2H), 4.22 (t, J=6.8 Hz, 2H), 5.08 (s, 2H).

Intermediate 87 perfluorobenzyl carbamate

Yield: 95%
1H NMR (CDCl$_3$, 400 MHz) δ 4.7 (s, 2H), 5.2 (s, 2H).

Intermediate 88 2-(2-(2-methoxyethoxy)ethoxy)ethyl carbamate

Yield: 21%
1H NMR (CDCl$_3$, 400 MHz) δ 3.40 (s, 3H), 3.54-3.77 (m, 10H), 4.21-4.30 (m, 2H).

Synthetic Procedure C

Intermediate 10: tert-butyl 4-(hydroxymethyl)phenylcarbamate

To a solution of p-aminobenzyl alcohol (38.2 mmol) in 100 ml dioxane were added triethylamine (114 mmol) and di-tert-butyldicarbonate (42.0 mmol) was added in portions. The mixture was stirred overnight at room temperature. The solvent was evaporated. EtOAc was added and washed with 2N HCl, saturated NaHCO$_3$ and brine solution. The organic layer was dried over Na$_2$SO$_4$ and evaporated to yield a brown oil.

Yield: 82%, MS (ESI) m/z 224.3 [M+H]$^+$
$^1$H-NMR (CDCl$_3$, 400 MHz) δ 1.54 (s, 9H), 4.65 (s, 2H), 6.54 (s, 1H), 7.22-7.43 (m, 4H).

Synthetic Procedure D

Intermediate 11: tert-Butyl 4-formylphenylcarbamate tert-butyl 4-(hydroxymethyl)phenylcarbamate (31.4 mmol) was added to a solution of dess-martinperiodinane (34.5 mmol) in 100 ml dry DCM. The solution was allowed to stir for 1 h at room temperature and was monitored with TLC (EtOAc/Hexane 1:1) and MS. The resulting solution was poured into a vigorously stirred saturated NaHCO$_3$ and Na$_2$S$_2$O$_3$ solution (1:1; 100 ml each) for 1 h. The organic layer was separated and washed with brine and dried over Na$_2$SO$_4$. The solvent was evaporated and a brown oily product was formed.

Yield: 91%, MS (ESI) m/z 222.6 [M+H]$^+$
$^1$H-NMR (CDCl$_3$, 400 MHz) δ 1.55 (s, 9H), 6.83 (s, 1H), 7.51-7.60 (m, 2H), 7.80-7.88 (m, 2H), 9.91 (s, 1H).

Synthetic Procedure E

Intermediate 1A benzyl((4-(tert-butoxycarbonyl)aminophenyl)(diphenoxyphosphoryl)methyl)carbamate To a solution of tert-butyl 4-formylphenylcarbamate (3.81 mmol), benzyl carbamate (3.81 mmol) and triphenyl phosphite (3.81 mmol) in DCM (40 ml) was added Cu(OTf)$_2$ (0.381 mmol). The resulting solution was stirred overnight at room temperature. The solvent was evaporated and the crude mixture was dissolved in MeOH, which was put overnight at −20° C. A precipitate was formed and filtered off.

Yield: 21%
$^1$H-NMR (DMSO-d$_6$, 400 MHz): δ 1.48 (s, 9H), 5.08 (m, 2H), 5.48 (m, 1H), 6.98 (d, J=7.6 Hz, 2H), 7.05 (d, J=8.0 Hz, 2H), 7.19 (m, 2H), 7.35 (m, 9H), 7.49 (m, 4H), 8.10 (d, J=9.6 Hz, 1H), 9.41 (s, 1H)

The following compounds were prepared in a similar way. The purification was done using flash chromatography (10% ethyl acetate in heptane to 100% ethyl acetate) but were analysed by UPLC only and used in subsequent reactions Intermediates: 12-16, 89

Synthetic Procedure F

Intermediate 2A: benzyl ((4-aminophenyl)(diphenoxyphosphoryl)methyl)carbamate 2,2,2-trifluoroacetate To a solution of benzyl-((4-(tert-butoxycarbonyl)aminophenyl)(diphenoxyphosphoryl)methyl)carbamate (0.049 mmol) in DCM (1 ml), TFA (12.98 mmol) was added. The solution was allowed to stir for 1 h at RT. Solvent was evaporated (TFA co-evaporated with hexane). The brown oily product was dissolved in a small amount of DCM and ether was added. A precipitate was formed. Ether was removed.

Yield: 96%
$^1$H-NMR (CDCl$_3$, 400 MHz): δ 5.07 (m, 2H), 5.44 (m, 1H), 6.82 (d, J=7.6 Hz, 2H), 6.96 (d, J=8.0 Hz, 2H), 7.05 (d, J=8.4 Hz, 2H), 7.19 (t, J=7.2 Hz, 2H), 7.33 (m, 9H), 7.41 (d, J=7.3 Hz, 2H), 8.76 (d, J=10.0 Hz, 1H)

The following compounds were prepared in a similar way but were only analysed via UPLC and used as such in subsequent Intermediates 17, 28, 31, 82.

For Final compound 114, 133-135 purification required reversed phase flash chromatography using a gradient (100% water to 30% MeOH in water).

Intermediate 19: 2-methoxyethyl ((4-aminophenyl)(diphenoxyphosphoryl)methyl)carbamate 2,2,2-trifluoroacetate Yield: 81%, MS (ESI) m/z 457.7 [M+H]$^+$
$^1$H NMR (CDCl$_3$, 400 MHz): δ 7.48-7.38 (m, 2H), 7.19 (dt, J=11.4, 7.3 Hz, 6H), 7.05 (d, J=8.0 Hz, 2H), 6.81 (d, J=8.3 Hz, 4H), 5.65 (s, 1H), 4.24 (s, 2H), 3.59 (s, 2H), 3.33 (s, 3H).

Intermediate 20: 2-phenoxyethyl ((4-aminophenyl)(diphenoxyphosphoryl)methyl)carbamate 2,2,2-trifluoroacetate Yield: 84%, MS (ESI) m/z 519.6 [M+H]$^+$
$^1$H NMR (CDCl$_3$, 400 MHz): δ 7.47 (s, 2H), 7.40 (s, 1H), 7.33 (s, 2H), 7.24 (s, 2H), 7.18 (s, 2H), 7.12 (s, 2H), 7.00 (s, 1H), 6.94 (s, 3H), 6.79 (s, 1H), 5.97 (s, 1H), 5.53 (s, 1H), 4.46 (s, 2H), 4.16 (s, 2H).

Final compound 5A: benzyl (diphenoxyphosphoryl)(4-guanidinophenyl)methylcarbamate 2,2,2-trifluoroacetate Yield: 47%, MS (ESI) m/z 531.6 [M+H]$^+$
$^1$H NMR (CD$_3$OD, 400 MHz) δ 5.05-5.27 (m, 2H), 5.63-5.76 (m, 1H), 6.95-7.16 (m, 4H), 7.15-7.46 (m, 13H), 7.62-7.77 (m, 2H), 8.75 (d, J=9.9 Hz, 1H).

Final compound 27: 2-(2-(prop-2-yn-1-yloxy)ethoxy)ethyl ((diphenoxyphosphoryl)(4-guanidinophenyl)methyl)carbamate 2,2,2-trifluoroacetate Yield: 80%, MS (ESI) m/z 567.7 [M+H]
$^1$H-NMR (CDCl$_3$, 400 MHz) δ 2.45 (t, J=2.4 Hz, 1H), 3.67 (d, J=9.9 Hz, 6H), 4.07 (s, 1H), 4.15 (d, J=2.4 Hz, 2H), 4.25 (s, 2H), 5.58 (dd, J=22.7, 9.1 Hz, 1H), 6.60 (s, 1H), 6.93-7.00 (m, 2H), 7.06-7.35 (m, 12H), 7.54 (d, J=7.9 Hz, 2H), 9.95 (br s, 1H).

Final compound 28: 2-(2-methoxyethoxy)ethyl((diphenoxyphosphoryl)(4-guanidinophenyl)methyl)carbamate 2,2,2-trifluoroacetate MS (ESI) m/z 543.7 [M+H]$^+$
$^1$H-NMR (CDCl$_3$, 400 MHz) δ 3.32 (s, 3H), 3.47-3.55 (m, 3H), 3.58-3.70 (m, 4H), 4.14-4.31 (m, 2H), 4.63 (d, J=34.4 Hz, 2H), 5.50-5.61 (m, 1H), 6.78 (s, 2H), 6.97 (s, 2H), 7.10 (d, J=8.1 Hz, 3H), 7.16 (s, 4H), 7.23 (s, 4H), 7.54 (s, 2H), 9.94 (s, 2H).

Final compound 29: 2-methoxyethyl ((diphenoxyphosphoryl)(4-guanidinophenyl)methyl)carbamate 2,2,2-trifluoroacetate MS (ESI) m/z 499.20 [M+H]$^+$
$^1$H-NMR (CDCl$_3$, 400 MHz) δ 11.48 (s, 1H), 10.07 (s, 1H), 7.54 (s, 2H), 7.32 (t, J=7.7 Hz, 3H), 7.23 (dd, J=17.8, 7.6 Hz, 4H), 7.17 (d, J=8.2 Hz, 2H), 7.10 (s, 2H), 6.97 (s, 2H), 6.37 (s, 1H), 5.59 (s, 1H), 4.25 (s, 2H), 4.02 (s, 2H), 3.90 (s, 1H), 3.36 (s, 3H).

Final compound 30: 2-phenoxyethyl((diphenoxyphosphoryl)(4-guanidinophenyl)methyl)carbamate 2,2,2-trifluoroacetate MS (ESI) m/z 561.7 [M+H]$^+$
$^1$H-NMR (CDCl$_3$, 400 MHz) δ 9.86 (s, 2H), 7.51 (s, 3H), 7.24 (s, 6H), 7.14 (s, 4H), 7.07 (s, 3H), 6.94 (s, 4H), 6.85 (s, 2H), 5.61 (s, 1H), 4.44 (s, 3H), 4.10 (s, 3H).

Final compound 31: 2-hexanamidoethyl ((diphenoxyphosphoryl)(4-guanidinophenyl)methyl)carbamate 2,2,2-trifluoroacetaat MS (ESI) m/z 582.7 [M+H]$^+$
$^1$H-NMR (CDCl$_3$, 400 MHz) δ 11.08 (s, 1H), 9.67 (s, 1H), 7.54 (s, 3H), 7.40-7.35 (m, 1H), 7.33 (s, 1H), 7.27-7.21 (m, 1H), 7.22-7.17 (m, 1H), 7.16 (s, 3H), 6.92 (s, 1H), 5.60 (s, 1H), 4.24 (s, 1H), 4.12 (s, 2H), 3.16 (s, 1H), 2.21 (s, 2H), 1.69 (s, 2H), 0.92-0.90 (m, 4H).

Final compound 92: Hexyl ((diphenoxyphosphoryl)(4-guanidinophenyl)methyl)carbamate Yield: 81%
MS (ESI): m/z 525.6 [M]+; Rt: 1.74 min (UPLC)
1H NMR (MeOD, 400 MHz) δ 0.81-0.96 (m, 3H), 1.22-1.40 (m, 9H), 1.46-1.64 (m, 4H), 3.70 (d, J=12.0 Hz, 1H), 4.07 (qt, J=11.0, 7.0 Hz, 2H), 5.50 (d, J=19.7 Hz, 1H), 5.66-5.78 (m, 1H), 6.52-6.75 (m, 2H), 6.84-7.00 (m, 2H), 7.03-7.46 (m, 12H).

Final Compound 107: 4,4,4-trifluorobutyl ((diphenoxyphosphoryl)(4-guanidinophenyl)methyl)carbamate Yield: 98%
MS (ESI): m/z 551.2 [M+H]$^+$; Rt: 1.64 min (UPLC)
1H NMR (DMSO-d$_6$, 400 MHz) δ 1.67-1.85 (m, 2H), 2.24-2.42 (m, 2H), 4.07 (ddt, J=39.0, 10.9, 6.4 Hz, 2H), 5.63 (dd, J=22.6, 10.2 Hz, 1H), 6.99-7.43 (m, 10H), 7.67-7.74 (m, 4H), 8.88 (dd, J=10.2, 1.7 Hz, 1H), 10.13 (s, 1H).

Final Compound 108: 2-(methylthio)ethyl ((diphenoxyphosphoryl)(4-guanidinophenyl)methyl)carbamate Yield: 25.7%
MS (ESI): m/z 515.2 [M+H]$^+$; Rt: 1.51 min (UPLC)
1H NMR (MeOD, 400 MHz) δ 2.13 (s, 3H), 2.64-2.78 (m, 2H), 4.26 (ddt, J=28.5, 11.1, 6.7 Hz, 2H), 5.69 (d, J=22.9 Hz, 1H), 7.04-7.43 (m, 12H), 7.70 (dd, J=8.5, 2.3 Hz, 2H).

Final Compound 109: (perfluorophenyl)methyl ((diphenoxyphosphoryl)(4-guanidinophenyl)methyl)carbamate Yield: 13.45%
MS (ESI): m/z 621.1 [M+H]$^+$; Rt: 1.73 min (UPLC)
1H NMR (DMSO-d$_6$, 400 MHz) δ 5.22 (d, J=12.4 Hz, 1H), 5.33 (d, J=12.3 Hz, 1H), 5.68 (d, J=22.5 Hz, 1H), 7.05 (dd, J=25.0, 8.0 Hz, 4H), 7.22 (t, J=7.4 Hz, 2H), 7.33 (td, J=8.3, 3.3 Hz, 6H), 7.69 (dd, J=8.6, 2.3 Hz, 2H), 8.57 (s, 1H).

Final Compound 110: 2-(2-(2-methoxyethoxy)ethoxy)ethyl ((diphenoxyphosphoryl)(4-guanidinophenyl)methyl)carbamate Yield: 31.5%
MS (ESI): m/z 587.2 [M+H]$^+$; Rt: 1.48 min (UPLC)

1H NMR (MeOD, 400 MHz) δ 3.34 (s, 3H), 3.48-3.57 (m, 2H), 3.54-3.74 (m, 8H), 4.17-4.32 (m, 2H), 5.69 (d, J=22.8 Hz, 1H), 6.99-7.49 (m, 12H), 7.66-7.80 (m, 2H).

Final Compound 114: 2-(2-methoxyethoxy)ethyl ((bis(4-acetamidophenoxy)phosphoryl)(4-guanidinophenyl)methyl) carbamate Yield: 80%

MS (ESI): m/z 657.3 [M+H]⁺; Rt: 1.23 min (UPLC)

1H NMR (MeOD, 400 MHz) δ 2.12 (s, 6H), 3.34 (s, 3H), 3.49-3.60 (m, 2H), 3.59-3.73 (m, 4H), 4.15-4.32 (m, 2H), 5.66 (d, J=22.8 Hz, 1H), 6.96-7.10 (m, 3H), 7.27-7.44 (m, 2H), 7.45-7.63 (m, 4H), 7.70 (ddd, J=11.1, 8.7, 2.3 Hz, 3H).

Final Compound 127: diphenyl ((4-guanidinophenyl)(phenylsulfonamido)methyl)phosphonate Yield: 87%

MS (ESI): m/z 537.1 [M+H]⁺; Rt: 1.54 min (UPLC)

1H NMR (MeOD, 400 MHz) δ 5.39 (d, J=25.8 Hz, 1H), 6.97-7.06 (m, 2H), 7.03-7.57 (m, 15H), 7.72-7.79 (m, 2H).

Final Compound 128: diphenyl ((4-guanidinophenyl)(phenylsulfonamido)methyl)phosphonate Yield: 91%

MS (ESI): m/z 537.1 [M+H]⁺; Rt: 1.54 min (UPLC)

1H NMR (MeOD, 400 MHz) δ 2.25 (s, 3H), 5.34 (dd, J=25.5, 10.3 Hz, 1H), 6.91-6.97 (m, 2H), 7.03-7.10 (m, 4H), 7.12 (d, J=8.0 Hz, 2H), 7.20 (q, J=7.6 Hz, 2H), 7.30-7.40 (m, 4H), 7.45-7.59 (m, 7H), 9.23 (dd, J=10.4, 2.0 Hz, 1H), 10.01 (s, 1H).

Final Compound 130: diphenyl ((4-guanidinophenyl)(4-methoxyphenylsulfonamido)methyl) phosphonate Yield: 85%

MS (ESI): m/z 605.1 [M+H]⁺; Rt: 1.72 min (UPLC)

1H NMR (MeOD, 400 MHz) δ 5.46 (d, J=25.6 Hz, 1H), 6.93-7.03 (m, 2H), 7.06 (dt, J=8.2, 1.4 Hz, 2H), 7.11-7.26 (m, 4H), 7.25-7.43 (m, 4H), 7.45-7.56 (m, 2H), 7.64 (d, J=8.3 Hz, 2H), 7.91-8.04 (m, 2H).

Final Compound 133: N-(6-(diethylamino)-9-(2-(4-(8-(4-(1-(diphenoxyphosphoryl)-1-(4-guanidinophenyl)-3-oxo-4,7,10-trioxa-2-azaundecan-11-yl)-1H-1,2,3-triazol-1-yl)octanoyl)piperazine-1-carbonyl)phenyl)-3H-xanthen-3-ylidene)-N-ethylethanaminium Yield: 12%

MS (ESI): m/z 1246.4 [M+H]⁺; Rt: 2.04 min (UPLC)

Final compound 134: 2-((1E,3E,5Z)-5-(1-(6-((2-(4-(1-(diphenoxyphosphoryl)-1-(4-guanidinophenyl)-3-oxo-4,7,10-trioxa-2-azaundecan-11-yl)-1H-1,2,3-triazol-1-yl)ethyl)amino)-6-oxohexyl)-3,3-dimethylindolin-2-ylidene)penta-1,3-dien-1-yl)-1,3,3-trimethyl-3H-indol-1-ium Yield: 15%

MS (ESI): m/z 1119.7 [M+H]⁺; Rt: 2.03 min (UPLC)

Final compound 135: 2-(2-((1-(13-oxo-17-((3aR,4R,6aS)-2-oxohexahydro-1H-thieno[3,4-d]imidazol-4-yl)-3,6,9-trioxa-12-azaheptadecyl)-1H-1,2,3-triazol-4-yl)methoxy)ethoxy)ethyl ((diphenoxyphosphoryl)(4-guanidinophenyl)methyl)carbamate Yield: 21%

MS (ESI): m/z 1112.1 [M+H]⁺; Rt: 1.58 min (UPLC)

Synthetic Procedure G

Intermediate 3A

N,N'-bis-Boc-1-guanylpyrazole (1.490 mmol) and triethylamine (2.98 mmol) were added to a solution of benzyl (4-aminophenyl)(diphenoxyphosphoryl)methylcarbamate) (1.528 mmol) in DCM (50 ml). The solution was allowed to stir overnight at room temperature. Solvent was evaporated and the residue was dissolved in EtOAc and washed with 1N HCl, sat NaHCO₃ and Brine solution. Organic layer was dried on anhydrous Na₂SO₄, filtered and concentrated in vacuo. The crude oil was purified with flash chromatography. (10% EtOAc in heptane to 100% EtOAc).

Yield: 57%, MS (ESI) m/z 731.3 [M+H]⁺

¹H-NMR (CDCl₃, 400 MHz) δ 1.56 (m, J=11.9 Hz, 18H), 5.08 (m, 2H), 5.56 (dd, J=22.0, 10.0 Hz, 1H), 5.79 (d, J=10.1 Hz, 1H), 6.93 (dt, J=8.4, 1.3 Hz, 2H), 7.07-7.40 (m, 13H), 7.49 (d, J=8.1 Hz, 2H), 7.66 (d, J=8.4 Hz, 2H), 10.39 (s, 1H), 11.63 (s, 1H).

Intermediates 22-26, 91, 103-106, 113, 123-126 were found pure using UPLC and were not further analysed at this stage and used as such in the next reaction step.

Synthetic Procedure H

Intermediate 61: 8-azidooctanoic acid

To a stirred solution of 8-bromooctanoic acid (2.241 mmol) in DMF (5 ml), was added sodium azide (4.48 mmol), and the mixture was heated at 85° C. for 3 h. The crude reaction mixture was diluted in DCM (50 ml) and this solution was washed with 0.1 N HCl. The organic layer was dried over Na₂SO₄. The solvent was evaporated. A yellow oily product was obtained.

Yield: 79%, MS (ESI) m/z 184.0 [M–H]⁻

¹H-NMR (CDCl₃, 400 MHz): δ 1.37 (m, 6H), 1.63 (m, 4H), 2.35 (t, J=7.2 Hz, 2H), 3.25 (t, J=6.8 Hz, 2H)

Synthetic Procedure I

Intermediate 63: N-(9-(2-(4-(8-azidooctanoyl)piperazine-1-carbonyl)phenyl)-6-(diethylamino)-3H-xanthen-3-ylidene)-N-ethylethanaminium chloride To a solution of 8-azidooctanoic acid (61) (1,828 mmol) in DMF (20 ml) was added TBTU (2,010 mmol) and DIPEA (5.48 mmol). The solution was stirred for 15 min at RT. N-(6-(diethylamino)-9-(2-(piperazine-1-carbonyl)phenyl)-3H-xanthen-3-ylidene)-N-ethylethanaminium chloride (62) (1,828 mmol) was added and the solution was allowed to stir overnight at RT. 200 ml water was added and the aqueous layer was extracted with DCM (2×). The resulting organic layer was extracted with 2N HCl, Saturated NaHCO₃ and Brine solution. The solvent was dried over Na₂SO₄, filtered and evaporated. The formed product was washed with hexane, EtOAc/Hexane ¼ and 2×20 ml EtOAc/Hexane 1/1.

A dark purple solid was formed. Product was dissolved in a small amount of DCM and added to a large amount of ether. A precipitate was formed.

Yield: 87%, MS (ESI) m/z 678.7 [M+H]$^+$ $^1$H-NMR (MeOD, 400 MHz): δ 1.31 (m, 18H), 1.56 (m, 4H), 2.34 (t, J=7.6 Hz, 2H), 3.27 (t, J=6.4 Hz, 2H), 3.35 (br s, 8H), 3.70 (q, J=7.2 Hz, 8H), 6.96 (d, J=2.4 Hz, 2H), 7.07 (dd, J=2.4 Hz and J=9.6 Hz, 2H), 7.28 (d, J=9.6 Hz, 2H), 7.52 (m, 1H), 7.70 (m, 1H), 7.77 (m, 2H)

LC-MS $t_r$ 21.5 min (100%)

HPLC (214 nm) $t_r$ 27.3 min (100%), HPLC (254 nm) $t_r$ 27.4 min (100%)

Synthetic Procedure J

Intermediate 66: (E)-N-((E)-3-(phenylamino)ally-lidene)benzenaminium chloride

To a solution of Malonaldehydebis(dimethylacetal) (0.03 mol) and concentrated HCl (4.25 mL) in water (85.5 mL), a solution of aniline (0.060 mol) and concentrated HCl (5 mL) in water (70 mL) was added drop wise. This mixture was allowed to stir at 70° C. for 17 hours. A precipitate was formed and filtered The product was obtained as an orange solid.

Yield: 77%, MS (ESI): m/z 223.6 [M]+en 221.6 [M−2H]—; Rt: 1.36 min (UPLC)

1H NMR (DMSO-d6, 400 MHz): δ 6.24 (t, 1H, J=11.6), 7.27 (t, 2H, J=7.4), 7.36 (d, 4H, J=8.0), 7.50 (t, 4H, J=7.7), 8.74 (br d, 2H, J=6.7), 12.09 (br s, 2H)

Synthetic Procedure K

Intermediate 67: 1,3,3-trimethyl-2-((1E,3E)-4-(phe-nylamino)buta-1,3-dienyl)-3H-indolium chloride To a solution of (E)-N-((E)-3-(phenylamino)allylidene) benzenaminium chloride (66) (9.66 mmol) in glacial acetic acid (25 ml) was added 1,3,3-trimethyl-2-methyleneindoline (9.66 mmol). The solution was left to stir overnight under reflux. The solvent was evaporated under reduced pressure. The obtained product was further purified using flash chromatography (5% methanol in EtOAc to 15% methanol in EtOAc) the final product was obtained as a red solid.

Yield: 49%, MS (ESI): m/z 303.4 [M+H]$^+$; Rt: 1.66 min (UPLC)

1H NMR (DMSO-d6, 400 MHz): δ 1.58 (s, 6H), 3.39 (s, 3H), 5.73 (d, 1H, J=12.59), 6.22 (dd, 1H, J=13.99 en 9.84), 6.93-6.96 (m, 2H), 7.13-7.24 (m, 4H), 7.33-7.37 (m, 3H), 7.71 (t, 1H, J=13.30), 8.42 (br d, 1H, J=6.32).

Synthetic Procedure L

Intermediate 68: 2-((1E,3E,5Z)-5-(1-(5-carboxypen-tyl)-3,3-dimethylindolin-2-ylidene)penta-1,3-di-enyl)-1,3,3-trimethyl-3H-indolium bromide To a solution of 1,3,3-trimethyl-2-((1E,3E)-4-(phe-nylamino)buta-1,3-dienyl)-3H-indolium chloride (67) (2.87 mmol),- and 1-(5-carboxypentyl)-2,3,3-trimethyl-3H-indol-1-ium bromide (2.87 mmol) in ethanol (70 ml) sodium acetate (6.51 mmol) was added. The solution was allowed to reflux for 18 hours. Solvent was evaporated and the obtained product was purified using flash chromatography (100% DCM to 10% methanol in DCM). The product was obtained as a blue powder. An additional purification was done using preparative TLC (5% methanol in DCM)

Yield: 49%, MS (ESI): m/z 483.3 [M]+; Rt: 1.91 min (UPLC) en 17.3 min (LC-MS)

$^1$H NMR (DMSO-d6, 400 MHz): δ 1.36-1.40 (m, 2H), 1.53-1.57 (m, 2H), 1.68 (s, 12H), 1.70-1.74 (m, 2H), 2.19 (t, 2H, J=7.3), 3.60 (s, 3H), 4.09 (t, 2H, J=7.0), 6.28 (dd, 2H, J=16.8 en 13.7), 6.56 (t, 1H, J=12.3), 7.22-7.28 (m, 2H), 7.35-7.45 (m, 4H), 7.61 (d, 2H, J=7.5), 8.33 (t, 2H, J=13.1), 11.98 (br s, 1H)

Synthetic Procedure M

Intermediate 70: 2-azidoethanamine

A solution of 2-aminoethylbromide hydrobromide (21.83 mmol) and sodium azide (65.5 mmol) in water (25 mL) was allowed to stir overnight at 70° C. This solution was brought to pH 12 with 2M sodium hydroxide. The obtained mixture was extracted with diethyl ether (3×50 mL). The organic layers were combined, dried over Na$_2$SO$_4$ and the solvent was evaporated to yield a yellow oil.

Yield: 43%

$^1$H NMR (CDCl$_3$, 400 MHz): δ 1.43 (s, 2H), 2.86 (t, 2H, J=5.7), 3.36 (t, 2H, J=5.7)

Synthetic Procedure N

Intermediate 71: 2-((1E,3E,5Z)-5-(1-(6-(2-azidoeth-ylamino)-6-oxohexyl)-3,3-dimethylindolin-2-ylidene)penta-1,3-dienyl)-1,3,3-trimethyl-3H-indo-lium tetrafluoroborate To a solution of 2-((1E,3E,5Z)-5-(1-(5-carboxypentyl)-3, 3-dimethylindolin-2-ylidene)penta-1,3-dienyl)-1,3,3-trim-ethyl-3H-indolium bromide (68) (0.19 mmol) in dry DMF (3 mL) was added TBTU (0.23 mmol) and DIPEA (0.23 mmol). This solution was allowed to stir for 1.25 hours and 2-azidoethanamine (70) (0.27 mmol) was added. The resulting mixture was allowed to stir overnight at room temperature. Solvent was removed and the product was purified using flash chromatography (100% DCM to 10% methanol in DCM). The product was obtained as a blue powder.

Yield: 43%, MS (ESI): m/z 551.4 [M]+; Rt: 1.86-1.98 min (UPLC), 19.00 min (LC-MS)

$^1$H NMR (MeOD, 400 MHz): δ 1.46 (m, 2H), 1.68 (m, 14H), 1.75 (m, 2H), 2.22 (t, J=7.2, 2H), 3.30 (s, 4H), 3.61 (s, 3H), 4.09 (t, J=7.6, 2H), 6.25 (dd, J=2.8 en J=13.6, 2H), 6.62 (t, J=12.4, 1H), 7.26 (m, 4H), 7.39 (m, 2H), 7.47 (d, J=7.6, 2H), 8.22 (t, J=13.6, 2H)

Synthetic Procedure O

Intermediate 74: 2,5-dioxopyrrolidin-1-yl 5-((3aS, 4S,6aR)-2-oxohexahydro-1H-thieno[3,4-d]imidazol-4-yl)pentanoate D-Biotin (0.819 mmol) and N-hydroxysuccinimide (0.819 mmol) were dissolved into anhydrous DMF (6 ml) at 70° C. while stirring. DCC (1.064 mmol) was added and the solution was stirred overnight at room temperature. The formed DCU was filtered off and the solvent was removed under reduced pressure. The residue was taken up into boiling isopropanol and the solution was allowed to cool down to RT. the target compound precipitated and the product was filtered off as a white solid.

Yield: 79%, MS (ESI) m/z 364.1 [M+Na]$^+$

NMR (DMSO-d$_6$, 400 MHz): δ 1.42-1.67 (m, 6H), 2.57-2.60 (d, J=12.4 Hz, 1H), 2.68 (t, J=7.3 Hz, 2H), 2.81-2.90

(m, 5H), 3.11 (m, 1H), 4.14-4.17 (m, 1H), 4.29-4.35 (m, 1H), 6.37 (s, 1H), 6.42 (s, 1H)

Synthetic Procedure P

Intermediate 75: N-(2-(2-(2-(2-azidoethoxy)ethoxy)ethoxy)ethyl)-5-((3aS,4S,6aR)-2-oxohexahydro-1H-thieno[3,4-d]imidazol-4-yl)pentanamide To a solution of 2-(2-(2-(2-azidoethoxy)ethoxy)ethoxy)ethanamine (0.293 mmol) in DMF (4 ml) triethylamine (0.293 mmol), followed by the addition of a solution of biotin-NHS 74 (0.293 mmol) in DMF (3 ml). The resulting solution was allowed to stir at room temperature for 15 hours. Solvent was evaporated under reduced pressure. The product was purified using flash chromatography (isocratic 10% methanol In EtOAc). A white solid was obtained
Yield: 69%, MS (ESI) m/z 467.3 [M+Na]$^+$
NMR (DMSO-$d_6$, 400 MHz): δ 1.29-1.64 (m, 6H), 2.07 (t, J=7.2 Hz, 2H), 2.59 (d, J=12.8 Hz, 1H), 2.82 (dd, J=5.2 Hz and J=12.4 Hz, 1H), 3.09 (m, 1H), 3.18 (m, 2H), 3.38 (m, 4H), 3.53 (m, 8H), 3.62 (m, 2H), 4.12 (m, 1H), 4.31 (m, 1H), 6.36 (s, 1H), 6.42 (s, 1H), 7.83 (t, J=5.6 Hz, 1H)

Synthetic Procedure Q

Intermediate 77: tert-butyl 2-(2-(2-(2-azidoethoxy)ethoxy)ethoxy)ethylcarbamate 2-(2-(2-(2-azidoethoxy)ethoxy)ethoxy)ethanamine (2 mmol) was dissolved in DCM (5 ml) and triethylamine (3.00 mmol). di-tert-butyl dicarbonate (2.2 mmol) dissolved in CH2Cl2 (1 mL) was added to the solution. The resulting mixture was stirred over the week end at room temperature. The crude reaction was then diluted with DCM and washed with water. The organic layer was dried over Na2SO4, filtered, and concentrated under reduced pressure. The product was purified using column chromatography: 30% EtOAc in hexane.
Yield: 71%
$^1$H NMR (CDCl3, 400 MHz) δ 1.47 (dt, J=6.6, 3.0 Hz, 9H), 2.07 (td, J=6.0, 3.0 Hz, 2H), 3.34 (d, J=7.3 Hz, 2H), 3.38-3.46 (m, 2H), 3.56 (q, J=5.4, 5.0 Hz, 2H), 3.61-3.75 (m, 10H).

Synthetic Procedure R

Intermediate 96 2-(methylthio)ethyl ((diphenoxyphosphoryl)(4-nitrophenyl)methyl)carbamate To a solution of 4-nitrobenzaldehyde (3.81 mmol), 2-(methylthio)ethyl carbamate (3.81 mmol) and triphenyl phosphite (3.81 mmol) in DCM (40 ml) was added Cu(OTf)$_2$ (0.381 mmol). The resulting solution was stirred overnight at room temperature. The solvent was evaporated and the crude mixture was purified using flash chromatography (10% ethyl acetate in heptane to 100% ethyl acetate)
Yield: 32.3%
MS (ESI): m/z 539.1 [M+H]$^+$; Rt: 2.08 min (UPLC)
1H NMR (DMSO-$d_6$, 400 MHz) δ 2.10 (s, 3H), 2.70 (t, J=6.6 Hz, 2H), 4.19 (ddt, J=17.8, 11.3, 5.5 Hz, 2H), 5.79-5.92 (m, 1H), 7.09 (ddt, J=15.8, 8.5, 1.2 Hz, 4H), 7.16-7.26 (m, 2H), 7.37 (tt, J=7.2, 1.7 Hz, 4H), 7.91-8.00 (m, 2H), 8.25-8.33 (m, 2H), 9.08 (dd, J=10.1, 2.1 Hz, 1H).
Intermediates 95, 97-98, 111 were found pure using UPLC and were not further analysed at this stage and used as such in the next reaction step. For Intermediate 111 tris(4-acetamidophenyl) phosphite was used instead of triphenyl phosphite.

Synthetic Procedure S

Intermediate 100 2-(methylthio)ethyl ((4-aminophenyl)(diphenoxyphosphoryl)methyl)carbamate 2-(methylthio)ethyl ((4-aminophenyl)(diphenoxyphosphoryl)methyl)carbamate (2.83 mmol) was dissolved in a 2:1 mixture of THF and saturated aqueous NH$_4$Cl (210 ml) and cooled to 0° C. Zinc dust (56.6 mmol) was added and the reaction mixture was vigorously stirred to keep the Zn dust in a suspension and to prevent it from caking on the bottom of flask.
The reaction mixture was stirred at room temperature for 1 hour. The reaction mixture was filtered on celite. The filtrate was extracted with EtOAC, washed with brine, dried over sodium sulfate and concentrated in vacuo to afford the product as a yellow oil
Yield: 100%
MS (ESI): m/z 473.2 [M+H]$^+$; Rt: 1.72 min (UPLC)
1H NMR (CD$_3$OD, 400 MHz) δ 2.12 (s, 3H), 2.71 (t, J=6.8 Hz, 2H), 4.24 (dddd, J=17.7, 13.4, 11.0, 6.8 Hz, 2H), 4.66 (s, OH), 5.47 (d, J=21.7 Hz, 1H), 6.67-6.82 (m, 2H), 6.88-7.06 (m, 2H), 7.05-7.39 (m, 10H).
Intermediates 99, 100, 101-102, 112, 119-122 were found pure using UPLC and were not further analysed at this stage and used as such in the next reaction step.

Synthetic Procedure T

Intermediate 116 diphenyl ((4-methylphenylsulfonamido)(4-nitrophenyl)methyl)phosphonate To a solution of 4-nitrobenzaldehyde (3.81 mmol), 4-methylbenzenesulfonamide (3.81 mmol) and triphenyl phosphite (3.81 mmol) in DCM (40 ml) was added Cu(OTf)$_2$ (0.381 mmol). The resulting solution was stirred overnight at room temperature. The solvent was evaporated and the crude mixture was purified using flash chromatography (10% ethyl acetate in heptane to 100% ethyl acetate)
Yield: 61%
MS (ESI): m/z 539.0 [M+H]$^+$; Rt: 2.07 min (UPLC)
1H NMR (MeOD, 400 MHz) δ 2.19 (s, 3H), 5.60 (dd, J=26.6, 10.4 Hz, 1H), 6.96 (d, J=8.0 Hz, 2H), 7.10 (dd, J=17.7, 8.0 Hz, 4H), 7.22 (dq, J=14.8, 8.3, 7.7 Hz, 2H), 7.36 (dt, J=21.5, 7.9 Hz, 4H), 7.51 (d, J=7.9 Hz, 2H), 7.69 (d, J=8.4 Hz, 2H), 8.00 (d, J=8.3 Hz, 2H).
Intermediates 115, 117-118 were found pure using UPLC and were not further analysed at this stage and used as such in the next reaction step.

Synthetic Procedure U

Intermediate 81 tert-butyl (2-(2-(2-(2-azidoethoxy)ethoxy)ethoxy)ethyl) carbamate (77) (1,304 mmol) was dissolved in Water/THF (40 mL, 1:1). 22 (1,304 mmol), copper(II) sulfate pentahydrate (0,782 mmol) and sodium ascorbate (3.13 mmol) were added. The reaction mixture was stirred for 5 h at room temperature. Afterwards, the reaction was quenched with water (20 mL) and extracted with DCM. The organic layers were dried over Na2SO4, filtered and concentrated under vacuum. The crude mixture was purified using flash chromatography (20% ethyl acetate in heptane to 100% ethyl acetate). The product was isolated as a white solid.

Yield: 58%

MS (ESI): m/z 1086.1 [M+H]$^+$; Rt: 2.47 min (UPLC)

1H NMR (MeOD, 400 MHz) δ 1.46 (d, J=19.2 Hz, 18H), 1.58 (d, J=5.4 Hz, 9H), 3.22 (td, J=5.7, 4.4 Hz, 2H), 3.49 (t, J=5.6 Hz, 2H), 3.52-3.73 (m, 14H), 3.88 (dd, J=5.6, 4.5 Hz, 2H), 4.20-4.28 (m, 2H), 4.52-4.66 (m, 4H), 5.63 (d, J=22.4 Hz, 1H), 6.97-7.05 (m, 2H), 7.10 (dq, J=7.7, 1.2 Hz, 2H), 7.15-7.26 (m, 2H), 7.28-7.39 (m, 4H), 7.54-7.68 (m, 4H).

Intermediates 78-80 were found pure using UPLC and were not further analysed at this stage and used as such in the next reaction step.

Synthetic Procedure V

Final Compound 83

2,2',2''-(10-(14-(4-(1-(diphenoxyphosphoryl)-1-(4-guanidinophenyl)-3-oxo-4,7,10-trioxa-2-azaundecan-11-yl)-1H-1,2,3-triazol-1-yl)-2-oxo-6,9,12-trioxa-3-azatetradecyl)-1,4,7,10-tetraazacyclododecane-1,4,7-triyl)triacetic acid In a round bottom flask washed with HCl (2N), rinsed with distilled water and dried with acetone (to avoid traces of metal), 82 (0,094 mmol) was dissolved in 3 mL CH3CN and 0.75 mL DMF. N-ethyl-N-isopropylpropan-2-amine (1,876 mmol) and was added. After 5 minutes and DOTA-NHS-ester (0,094 mmol) was added. The reaction was stirred at room temperature for 2 hours. The solvents were removed under reduced pressure. The crude mixture was dissolved in water (20 ml). After filtration over an activated (10 mL EtOH+10 ml H$_2$O) Sep Pak plus column (Waters) and washing with 20 mL of water. The compound was eluted with 2×10 ml of methanol. After evaporation of the methanol the product was isolated as a white solid.

Yield: 63.6%

MS (ESI): m/z 1172.2 [M+H]$^+$; Rt: 1.29 min (UPLC)

1H NMR (MeOD, 400 MHz) δ 1.78-1.96 (m, 2H), 2.68 (td, J=7.2, 4.2 Hz, 2H), 2.95-3.14 (m, 10H), 3.22-3.65 (m, 26H), 3.73 (s, 3H), 3.83-4.14 (m, 3H), 4.49-4.71 (m, 3H), 7.24 (td, J=10.3, 8.4, 5.3 Hz, 8H), 7.40 (t, J=7.8 Hz, 6H), 7.67-7.81 (m, 1H).

Synthetic Procedure W

Final Compound 132 diphenyl ((4-guanidinophenyl)(4-methoxyphenylsulfonamido)methyl)phosphonate

Compound 3A (1.3 mmol) was stirred in 10 ml of in a solution of HBr in acetic acid (33%) for 2 hours at room temperature. The solvents were evaporated under reduced pressure. The crude mixture was washed with diethyl ether. The compound precipitated as an off-white solid and was filtered.

Yield: 85%

MS (ESI): m/z 397.1 [M+H]$^+$; Rt: 1.15 min (UPLC)

1H NMR (DMSO-d$_6$, 400 MHz) δ 5.72 (d, J=18.5 Hz, 1H), 6.99-7.06 (m, 2H), 7.12-7.18 (m, 2H), 7.20-7.31 (m, 2H), 7.33-7.48 (m, 6H), 7.56 (s, 3H), 7.68-7.80 (m, 2H), 9.45 (s, 2H), 9.89 (s, 1H).

Synthesized compounds of the invention include:

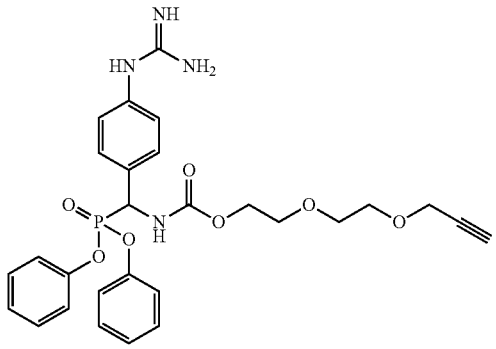

27

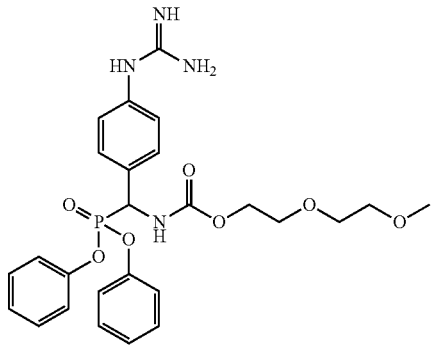

28

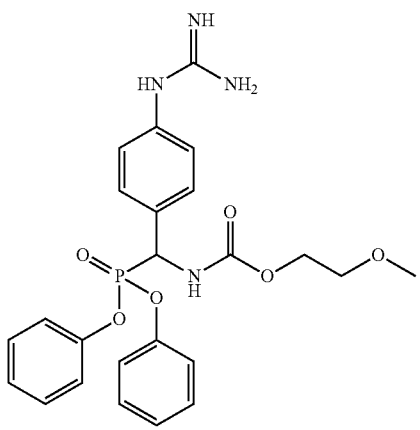

29

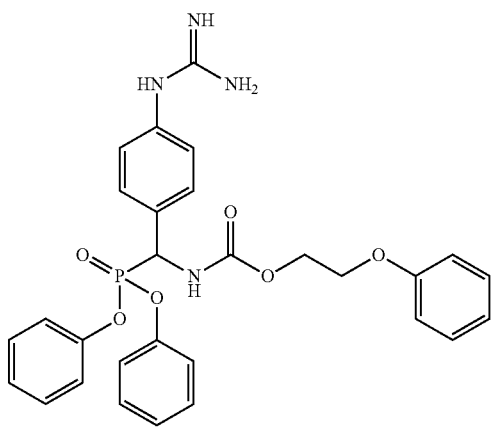

30

-continued
31
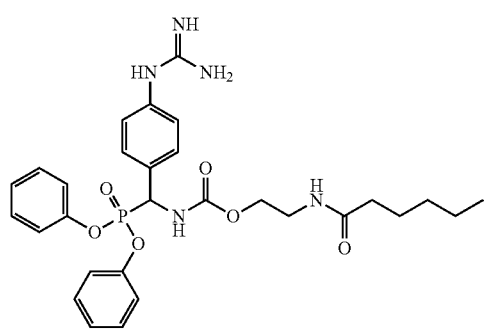
92
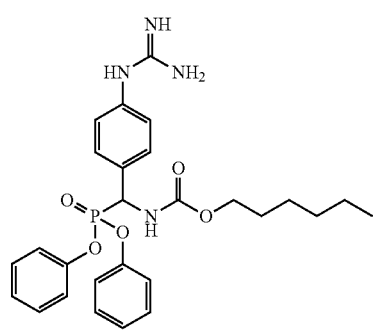
107
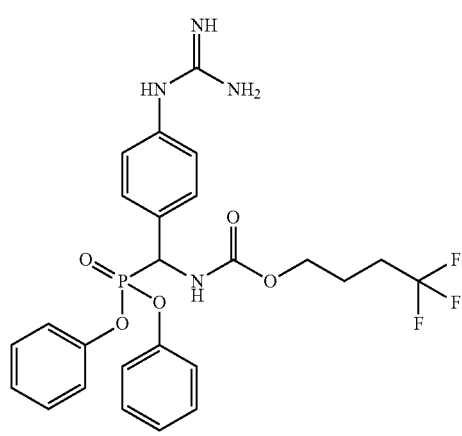
108
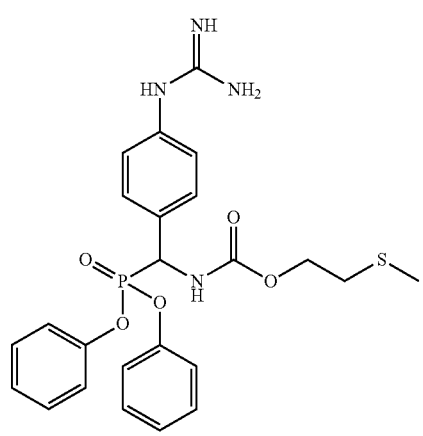
109
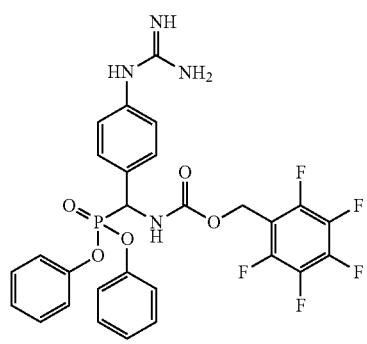
110
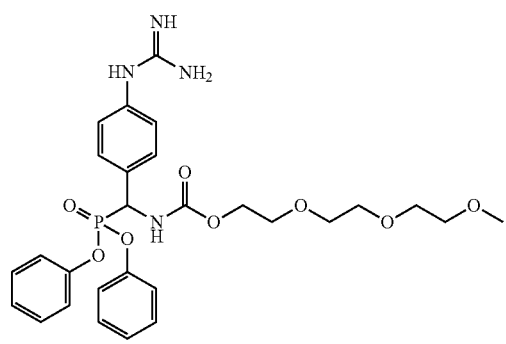
114
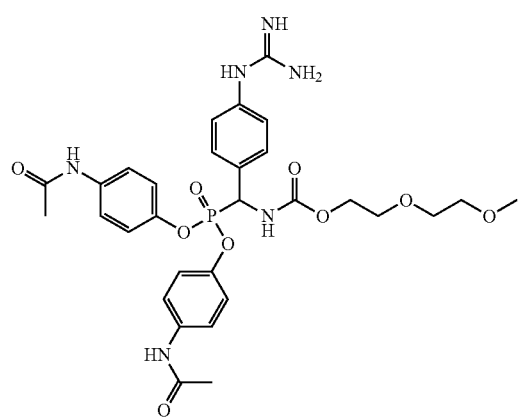
127
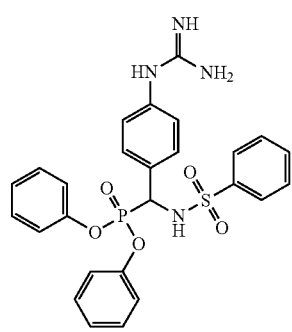

-continued
128 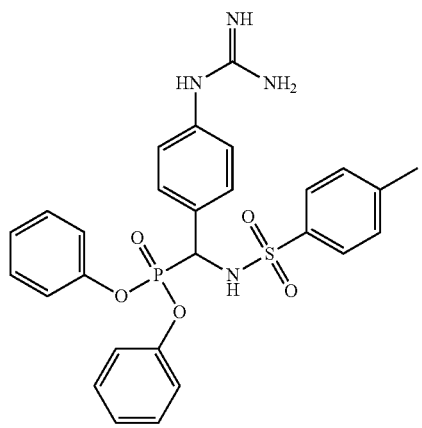
130 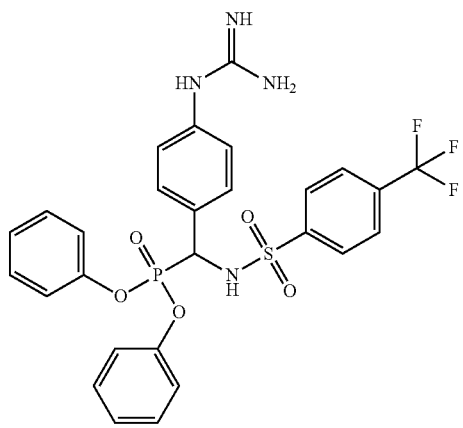
132 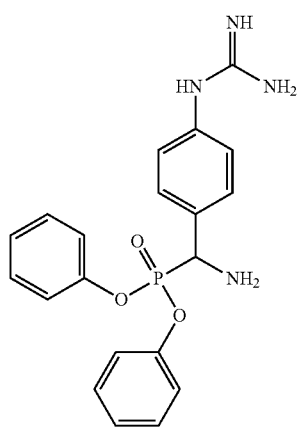
133 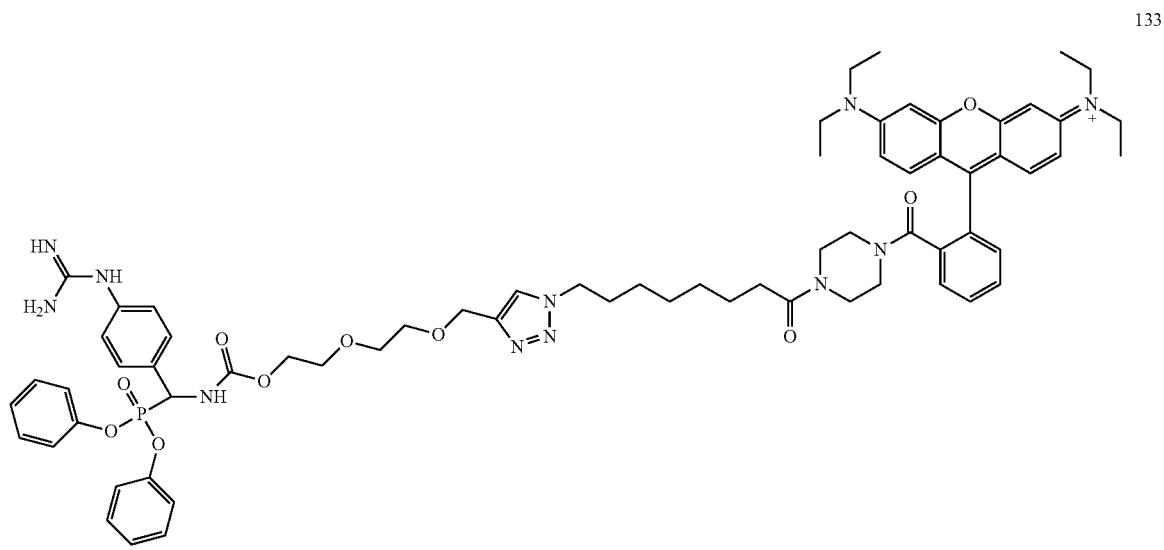

134
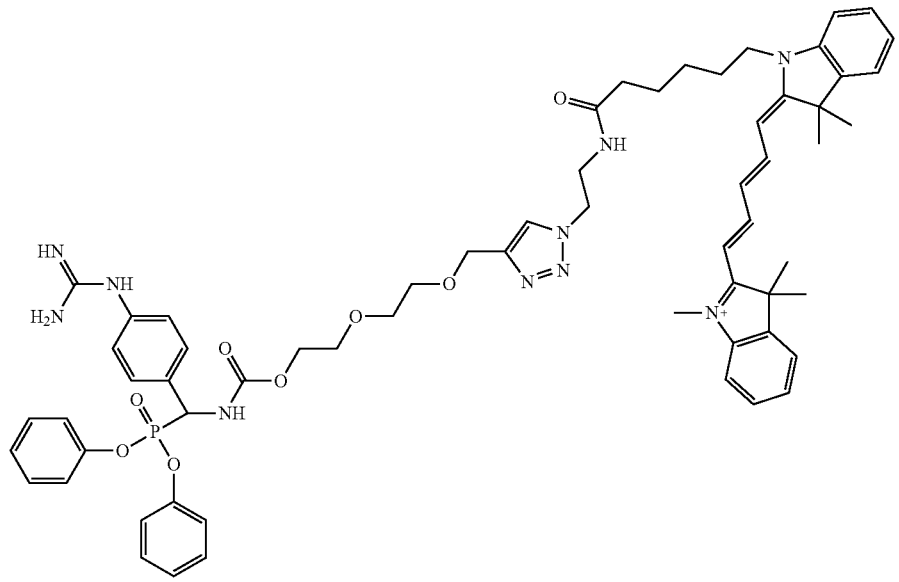
135
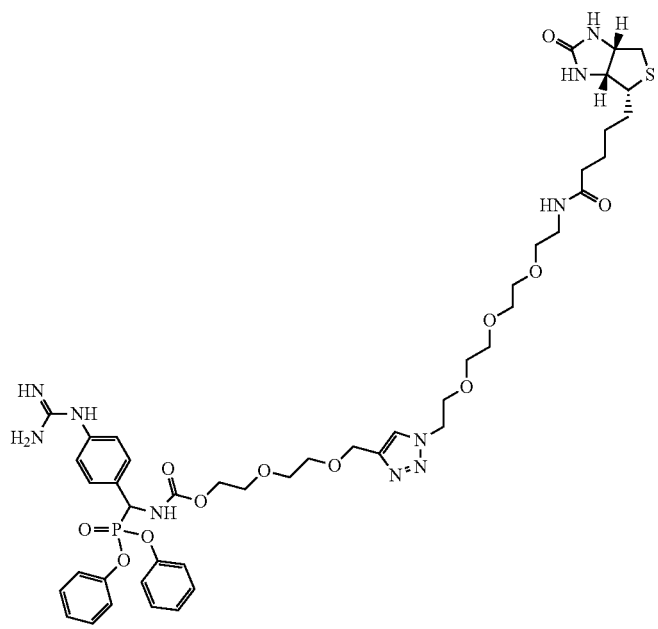
83
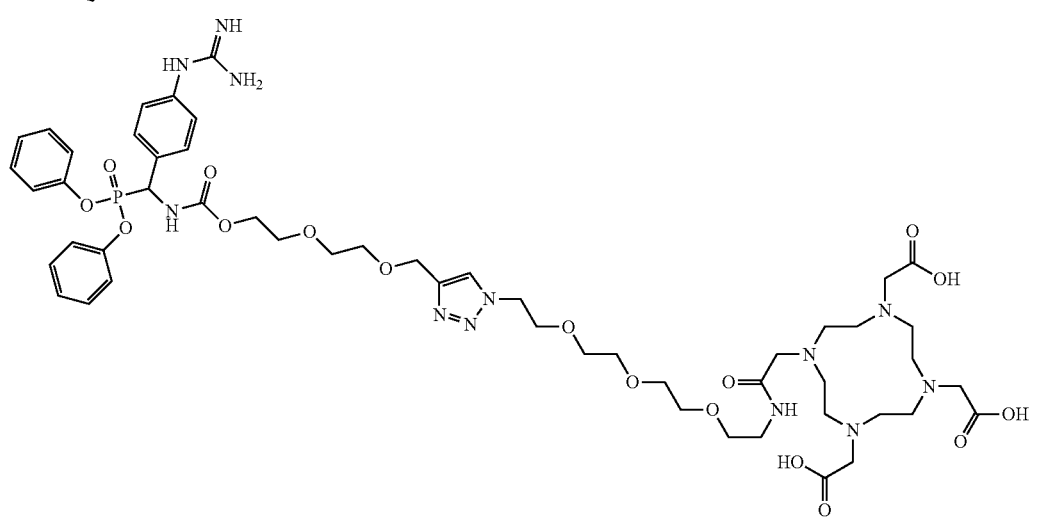

A particularly interesting group of compounds of the present invention are those selected from the group consisting of:
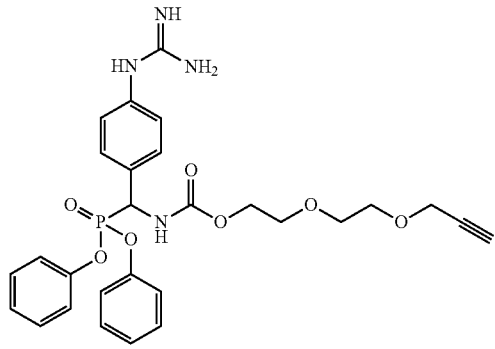
27
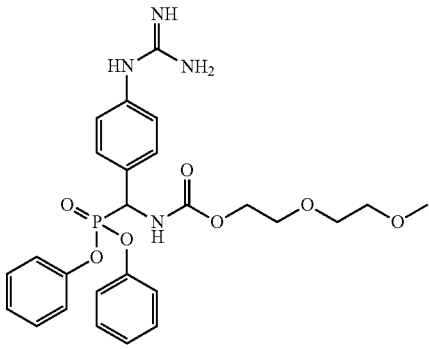
28
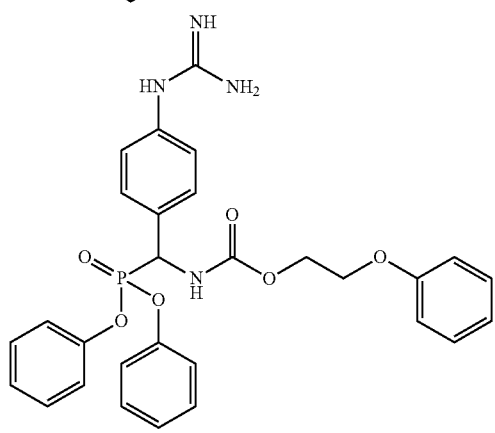
30
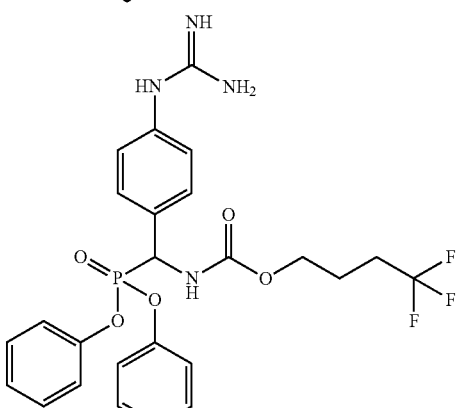
107
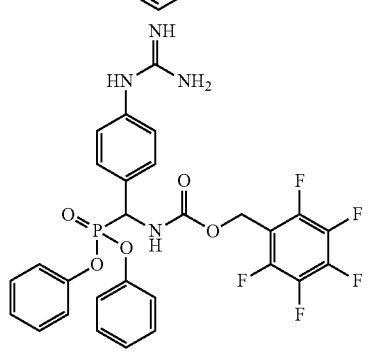
109
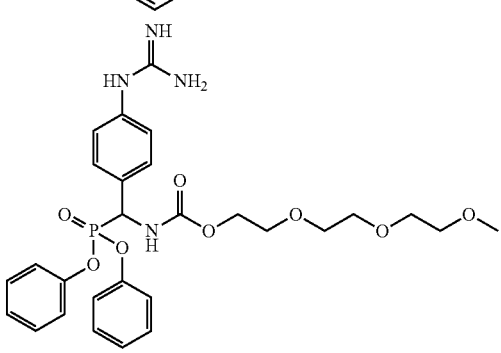
110
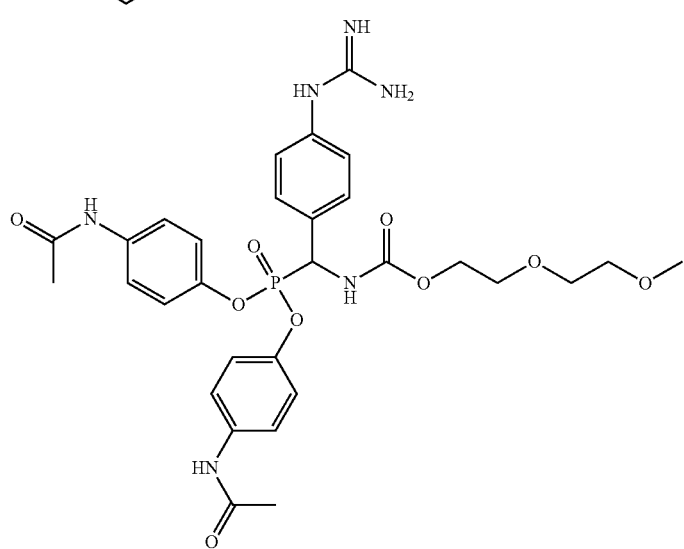
114

-continued
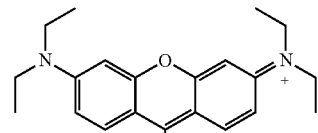
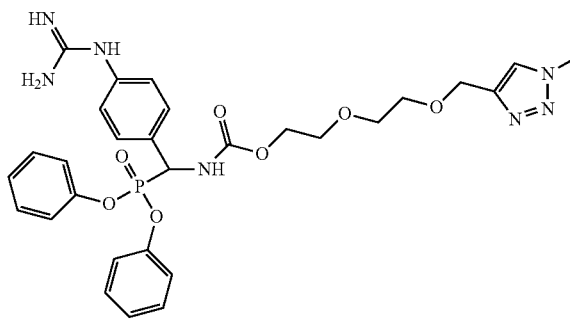
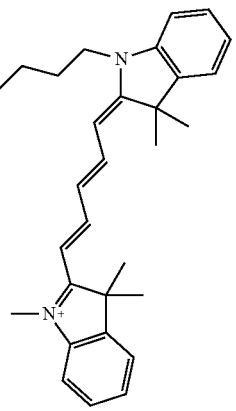
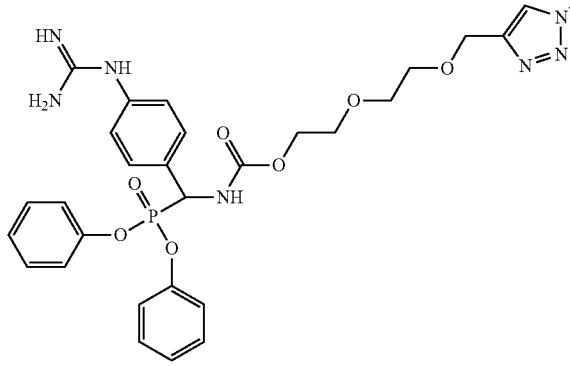
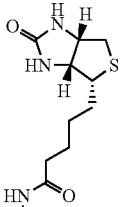
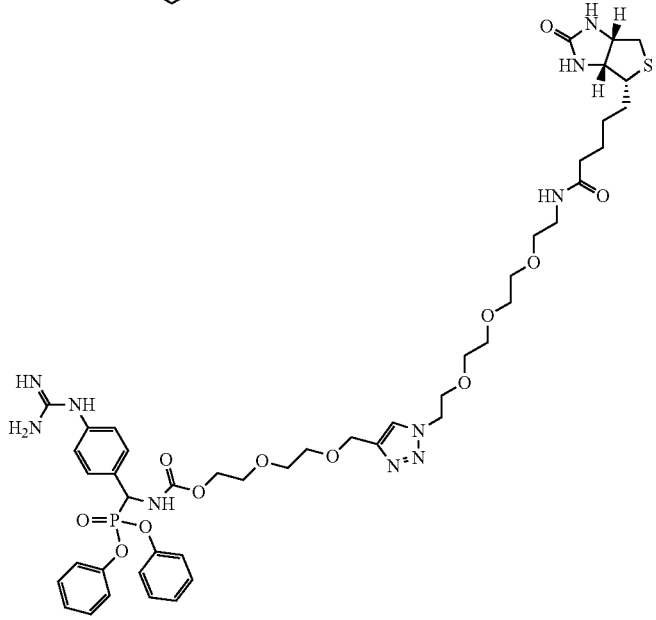

Biochemical Evaluation
Materials and Methods

For KLK4 Enzymatic activity was measured at 37° C. in a Biotek Synergy Mx Monochromator-Based Multi-Mode Microplate Reader using the fluorogenic substrate Bachem I-1120 (Boc-Val-Pro-Arg-AMC), with a Km of 20 µM.

The substrate was obtained form Bachem and the enzyme was provided by Viktor Magdolen (TUM). The reaction was monitored with an excitation wavelength of 355 nm and emission wavelength of 460 nm. The initial rate was determined between 2500000 and 4500000 mRFU/min. The reaction mixture contained 25 µM substrate and approximately 1 mU of enzyme in 145 µL of buffer in a final volume of 2000 µL. A 50 mM Tris buffer, pH 8.3, was used. From each inhibitor concentration, 5 µL was added, obtaining a final concentration from 0 to 250 µM in a total volume of 0.2 mL. Activity measurements were routinely performed in duplicate. The $IC_{50}$ value is defined as the concentration of inhibitor required to reduce the enzyme activity to 50% after a 15 min pre-incubation with the enzyme at 37° C. before addition of the substrate. $IC_{50}$ values were obtained by fitting the data with the four-parameter logistics equation using Grafit 7.

$$v = \frac{v\text{range}}{1 + e^{sbi|I_0/IC_{50}|}} + \text{background}$$

where s=slope factor, v=rate, $I_0$=inhibitor concentration, and range=the fitted uninhibited value minus the background. The equation assumes they falls with increasing x.

Inhibitor stock solutions were prepared in DMSO and stored at −20° C. Because the compounds described in this paper completely inactivate KLK4 following pseudo first-order kinetics, the $IC_{50}$ value is inversely correlated with the second-order rate constant of inactivation. For a simple pseudo first-order inactivation process, the activity after incubation with inhibitor $(v_i)$ varies with the inhibitor concentration (i), as described in the following equation: $v_i = v_0 \times e^{-k} t$, where $v_o$ is the activity in absence of inhibitor, k is the second-order rate constant of inactivation, and t is the time. The inactivation rate constant was determined from the time course of inhibition.

The inhibitor was mixed with the substrate (250 µM final concentration), and the buffer solution with the enzyme was added at the time zero. The inhibitor concentrations were chosen to obtain total inhibition of the enzyme within 20 min. The progress curves show the absorbance of aminomethylcoumarine produced as a function of time. Initially, no inhibitor is bound to the enzyme, and the tangent to the progress curve (dA/dt) is proportional to the concentration of the free enzyme. The concentration of free enzyme decreases over time due to the kinetics of inhibitor binding, as described above. Progress curves were recorded in pseudo first-order conditions ($[I]_0 \gg [E]_0$) and with less than 10% conversion of the substrate during the entire time course. In these conditions, dA/dt decreases exponentially with time. The progress curves were fitted with the integrated rate equation to yield a value for $k_{obs}$, a pseudofirst-order rate constant $$A_t = v_0[1 - e^{-k_{obs}t}]/k_{obs} + A_0$$

where $A_t$=absorbance at time t, $A_0$=absorbance at time zero, and $v_0$=uninhibited initial rate.

The apparent second-order rate constant ($k_{app}$) was calculated from the slope of the linear part of the plot of $k_{obs}$ versus the inhibitor concentration ($[I]_0$). In case of competition between the inhibitor and the substrate, $k_{app}$ is smaller than the "real" second order rate constant k discussed above because a certain fraction of the enzyme is present as an enzyme-substrate complex. $k_{app}$ depends on the substrate concentration used in the experiment, as described by Lambeir et al. (Lambeir, Borloo et al. 1996).

The $IC_{50}$ values For KLK1, KLK2 and KLK8 were obtained in a similar way. For plasmin, tPA, thrombin, Fxa, HNE, Plasma kallikrein Chromogenic substrates were used (absorption: 405 nm). (KLK2, KLK4, KLK8 were supplied by Viktor Magdolen TUMunich (TUM)).

| Target | Supplier | Substrate | Buffer |
| --- | --- | --- | --- |
| Plasmine (human plasma) | Sigma-Aldrich | Biophen CS-21(66) (pyroGlu-Pro-Arg-pNA•HCl) Km: 400 µM | Tris buffer pH 7.4 |
| uPA (recombinant) | Nodia | Biophen CS-61(44) (PyroGlu-Gly-Arg-pNa•HCl) Km: 80 µM | Tris buffer pH 8.8 |
| tPA (recombinant) | Nodia | Biophen CS-05(88) (H-D-Ile-Pro-Arg-pNa•2HCl) Km: 1 mM | Tris buffer pH 8.3 |
| Thrombine (human plasma) | Sigma-Aldrich | Biophen CS-21(66) (pyroGlu-Pro-Arg-pNA•HCl) Km: 150 µM | Tris buffer pH 8.3 |
| FXa | Nodia | Biophen CS-11(32) (Suc-Ile-Glu(γPip)Gly-Arg-pNa, HCl) Km: 1.5 mM | Tris buffer pH 8.3 |
| Neurtophil Elastase(human) | Enzo-life sciences | Enzo MeOSuc-Ala-Ala-Pro-Val-pNA Km: 125 µM | Tris buffer pH 7.8 |
| PlasmaKLK (human plasma) | Sigma-Aldrich | Biophen CS-31(02) D-Pro-Phe-Arg-pNa•2HCl km: 200 µM | Tris buffer pH 7.8 |
| KLK1 (human) | Prospec | Bachem I-1295 H-Pro-Phe-Arg-AMC km: 20 µM | Tris buffer pH 7.8 |
| KLK2 (human) | TUM | Bachem I-1295 H-Pro-Phe-Arg-AMC km: 20 µM | Tris buffer pH 8.3 |
| KLK8 (human) | TUM | Bachem I-1120 Boc-Val-Pro-Arg-AMC km: 20 µM | Tris buffer pH 8 |

Results

Results of $IC_{50}$ measurements are shown in Table 2. As can be seen, comparative compound 5a, originally reported as a uPA inhibitor (Sieniczyk et al., 2006), lacking a heteroatom in the tail, was now for the first time found to be KLK4 active, however, it is not selective over other kallikreins (e.g. KLK2, KLK1, KLK8) and on top of that shows reversible binding to KLK4.

On the other hand, the compounds of the invention display strong selectivity of KLK4 over other kallikreins and other peptidases, and/or dependent on the specifically selected tail, are found to be irreversible KLK4 inhibitors.

Furthermore, compounds of the invention show very low uPA activity, which is attributed to the difference of the phenyl guanidine in the compounds of the invention, compared to the benzyl guanidine group in prior art uPA inhibitors. For comparison, compound 56 of WO2012152807 (uPA2) differs from compound 27 of the invention only in this respect. Nonetheless, this difference causes a xxx-fold drop of uPA $IC_{50}$.

Even more a comparative compound lacking both a heteroatom in the tail and having a benzyl guanidine instead of a phenyl guanidine (uPA1) was found to be a non-selective reversible KLK4 inhibitor.

These data therefore confirm that the compounds of the invention having a phenyl guanidine moiety, a biphenyl phosphonate moiety and a heteroatom in the tail are active and selective KLK4 inhibitors, and/or dependent on the specifically selected tail results in irreversible KLK4 binders. This is in contrast to prior art compounds which have a benzyl guanidine moiety° and/or which lack a heteroatom in the tail*, which were found to be non-selective reversible KLK4 inhibitors.

TABLE 2

$IC_{50}$ values of the synthesized compounds:

| Nr | Irreversible/ $k_{app}$ KLK4 ($M^{-1}s^{-1}$) | KLK4 | KLK2 | KLK1 | KLK8 | uPA | tPA | THR | PLM | FXa | pKLK | HNE | AcHE | MAT |
|---|---|---|---|---|---|---|---|---|---|---|---|---|---|---|
| | | | | | | IC50 (µM) | | | | | | | | |
| 5a* | NO | +++ | +++ | ++ | + | − | --- | --- | − | − | − | -- | -- | − |
| 27 | Yes/ $16 \times 10^3 \pm 3 \times 10^3$ | +++ | + | − | -- | − | --- | --- | ND | -- | − | − | -- | − |
| 28 | Yes/ $34 \times 10^3 \pm 11 \times 10^3$ | +++ | ++ | -- | -- | -- | --- | --- | -- | -- | -- | -- | -- | − |
| 29 | N/A | ++ | ++ | -- | -- | -- | --- | --- | -- | -- | -- | − | -- | − |
| 30 | Yes/ $15 \times 10^3 \pm 2 \times 10^3$ | +++ | ++ | − | -- | − | --- | --- | -- | -- | -- | -- | -- | − |
| 31 | NO | ++ | ND | -- | -- | -- | --- | --- | -- | -- | -- | -- | -- | − |
| 83 | NO | +++ | ND | − | − | − | -- | -- | − | -- | -- | ND | -- | − |
| 92* | NO | +++ | ++ | + | − | − | − | --- | − | − | − | − | -- | − |
| 107 | Yes | +++ | ++ | − | − | − | ND | ND | -- | ND | ND | ND | ND | − |
| 108 | NO | +++ | ++ | + | + | − | ND | ND | -- | ND | ND | ND | ND | − |
| 109 | Yes/ $1.04 \times 10^4 \pm 0.4 \times 10^4$ | +++ | ++ | ++ | + | − | ND | ND | -- | ND | ND | ND | ND | + |
| 110 | Yes/ $1.96 \times 10^4 \pm 0.2 \times 10^4$ | +++ | ND | − | + | − | ND | ND | -- | ND | ND | ND | ND | − |
| 114 | Yes/ $1.01 \times 10^4 \pm 0.05 \times 10^4$ | +++ | ++ | − | + | − | ND | ND | -- | ND | ND | ND | ND | + |
| 127* | N/A | − | ND | ND | ND | − | − | − | − | − | − | ND | ND | − |
| 128* | NO | ++ | ND | ND | ND | − | − | − | − | − | − | ND | ND | ND |
| 130 | NO | +++ | ND | ND | ND | ND | ND | ND | ND | ND | ND | ND | ND | ND |
| 132* | NO | ++ | ND | − | ND | − | − | − | − | − | − | ND | ND | ND |
| 133 | ND | +++ | ND | ND | ND | − | --- | -- | − | -- | -- | -- | ND | − |
| 134 | Yes/ $2.24 \times 10^3 \pm 0.3 \times 10^3$ | ++ | ND | − | − | − | --- | -- | -- | -- | -- | -- | -- | − |
| 135 | Yes/ $9.1 \times 10^3 \pm 0.2 \times 10^3$ | +++ | ND | − | ND | − | ND | -- | -- | -- | -- | ND | ND | − |
| UPA 1*° | No | +++ | +++ | − | +++ | +++ | -- | + | − | -- | − | − | -- | ++ |
| UPA 2° | No | ND | ND | ND | ND | +++ | --- | -- | − | --- | -- | ND | ND | ++ |

*comparative examples which differ in the absence of a heteroatom in the tail
°comparative examples which differ in the presence of a benzyl guanidine instead of phenylguanidine
THR: Thrombin;
PLM: Plasmin;
pKLK: Plasma KLK;
MAT: Matriptase
+++: <0.1 µM;
++: 0.1-1 µM;
+: 1-2.5 µM;
−: 2.5-10 µM;
--: 10-250 µM;
>250 µM: ---
ND: not determined
N/A: not applicable ($IC_{50}$ >1 µM)

TABLE 2-continued

IC$_{50}$ values of the synthesized compounds:

| Nr | Irreversible/ $k_{app}$ KLK4 (M$^{-1}$s$^{-1}$) | IC50 (µM) | | | | | | | | | | | |
|---|---|---|---|---|---|---|---|---|---|---|---|---|---|
| | | KLK4 | KLK2 | KLK1 | KLK8 | uPA | tPA | THR | PLM | FXa | pKLK | HNE | AcHE | MAT |

UPA1

UPA2

REFERENCES

Blum, G., et al. (2009). "Comparative Assessment of Substrates and Activity Based Probes as Tools for Non-Invasive Optical Imaging of Cysteine Protease Activity." Plos One 4(7).

Brown, C. M., et al. (2011). "Peptide Length and Leaving-Group Sterics Influence Potency of Peptide Phosphonate Protease Inhibitors." Chemistry & Biology 18(1): 48-57.

Drag, M. and J. Oleksyszyn (2005). "Synthesis of alpha(1)-(Cbz-aminoalkyl)-alpha 2-(hydroxyalkyl)phosphinic esters." Tetrahedron Letters 46(19): 3359-3362.

Drag, M., et al. (2005). "alpha-aminoalkylphosphonates induced apoptosis in human tumor cell lines." Polish Journal of Chemistry 79(3): 593-602.

Goettig, P., et al. (2010). "Natural and synthetic inhibitors of kallikrein-related peptidases (KLKs)." Biochimie 92(11): 1546-1567.

Grzywa, R., et al. (2007). "The molecular basis of urokinase inhibition: from the nonempirical analysis of intermolecular interactions to the prediction of binding affinity." Journal of Molecular Modeling 13(6-7): 677-683.

Haedke, U., et al. (2013). "Tuning probe selectivity for chemical proteomics applications." Current Opinion in Chemical Biology 17(1): 102-109.

Joossens, J., et al. (2004). "Development of irreversible diphenyl phosphonate inhibitors for urokinase plasminogen activator." Journal of Medicinal Chemistry 47(10): 2411-2413.

Joossens, J., et al. (2007). "Small, Potent, and Selective Diaryl Phosphonate Inhibitors for Urokinase-Type Plasminogen Activator with In Vivo Antimetastatic Properties." Journal of Medicinal Chemistry 50(26): 6638-6646.

Jung, M. E. and W.-J. Kim (2006). "Practical syntheses of dyes for difference gel electrophoresis." Bioorganic & Medicinal Chemistry 14(1): 92-97.

Lambeir, A.-M., et al. (1996). "Dipeptide-derived diphenyl phosphonate esters: mechanism-based inhibitors of dipeptidyl peptidase IV." Biochimica et Biophysica Acta (BBA)—General Subjects 1290(1): 76-82.

Nguyen, T. and M. B. Francis (2003). "Practical Synthetic Route to Functionalized Rhodamine Dyes." Organic Letters 5(18): 3245-3248.

Oikonomopoulou, K., et al. (2008). "Immunofluorometric activity-based probe analysis of active KLK6 in biological fluids." Biological Chemistry 389(6): 747-756.

Pan, Z. Y., et al. (2006). "Development of activity-based probes for trypsin-family serine proteases." Bioorganic & Medicinal Chemistry Letters 16(11): 2882-2885.

Schmitt, M., et al. (2013). "Emerging clinical importance of the cancer biomarkers kallikrein-related peptidases (KLK) in female and male reproductive organ malignancies." Radiology and Oncology 47(4): 319-329.

Sienczyk, M. and J. Oleksyszyn (2004). "A convenient synthesis of new alpha-aminoalkylphosphonates, aromatic analogues of arginine as inhibitors of trypsin-like enzymes." Tetrahedron Letters 45(39): 7251-7254.

Sienczyk, M. and J. Oleksyszyn (2006). "Inhibition of trypsin and urokinase by Cbz-amino(4-guanidino-phenyl) methanephosphonate aromatic ester derivatives: The influence of the ester group on their biological activity." Bioorganic & Medicinal Chemistry Letters 16(11): 2886-2890.

Sienczyk, M. and J. Oleksyszyn (2009). "Irreversible Inhibition of Serine Proteases—Design and In Vivo Activity of Diaryl alpha-Aminophosphonate Derivatives." *Current Medicinal* Chemistry 16(13): 1673-1687.

van der Veken et al. (2005). "Lewis acid catalyzed synthesis of N-protected diphenyl 1-aminoalkylphosphonates." *Synthesis: Journal of synthetic organic chemistry* 634-638

The invention claimed is:

1. A compound of formula I or a stereoisomer, tautomer, racemic or salt thereof,

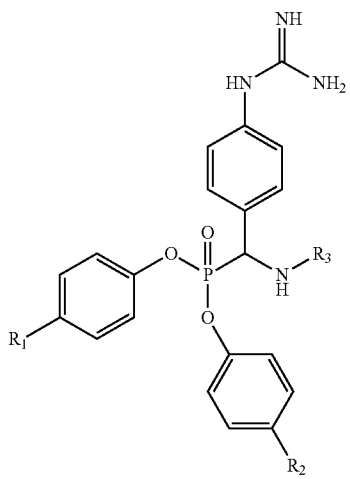

Wherein

R$_1$ and R$_2$ are each independently —H, —R', —C$_{1-6}$alkyl, —C$_{1-6}$alkenyl, or —C$_{1-6}$alkynyl; wherein said —C$_{1-6}$alkyl, —C$_{1-6}$alkenyl, and —C$_{1-6}$alkynyl is optionally substituted with one or more R' groups and wherein optionally one carbon atom in said —C$_{1-6}$alkyl, —C$_{1-6}$alkenyl, and —C$_{1-6}$alkynyl is replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

R$_3$ is —C(=O)OR$_4$, —C(=O)NR"R$_5$, —S(=O)(=O)R$_6$, —C(=O)R$_7$, or R$_8$;

R$_4$, R$_5$, R$_6$, R$_7$, and R$_8$ are L$_1$-Cy-L$_2$-Det;

L$_1$ is a direct bond or an optionally substituted group selected from —C$_{1-20}$alkyl, —C$_{1-20}$alkenyl, and —C$_{1-20}$alkynyl, wherein said —C$_{1-20}$alkyl-, —C$_{1-20}$alkenyl-, and —C$_{1-20}$alkynyl- is optionally substituted with one or more R' groups; and wherein optionally one or more non-adjacent carbon atoms in said —C$_{1-20}$alkyl-, —C$_{1-20}$alkenyl-, or —C$_{1-20}$alkynyl- are replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

Cy is selected from a direct bond, cycloalkyl, heterocyclyl, aryl, and heteroaryl; wherein said cycloalkyl, heterocyclyl, aryl, and heteroaryl is optionally substituted with one or more R' groups;

L$_2$ is a direct bond or an optionally substituted group selected from —C$_{1-20}$alkyl, —C$_{1-20}$alkenyl, and —C$_{1-20}$alkynyl; wherein said —C$_{1-20}$alkyl-, —C$_{1-20}$alkenyl-, and —C$_{1-20}$alkynyl- is optionally substituted with one or more R' groups; and wherein optionally one or more non-adjacent carbon atoms in said —C$_{1-20}$alkyl-, —C$_{1-20}$alkenyl-, or —C$_{1-20}$alkynyl- are replaced by O, NR", S, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR";

Det is hydrogen or a detectable label;

R' is each independently selected from the group consisting of amino, hydroxyl, thiol, cyano, nitro, oxo, and halo;

R" is at each instance each independently selected from hydrogen and C$_{1-6}$alkyl;

wherein at least one heteroatom is present in -L$_1$-Cy-L$_2$-;

wherein R$_7$ is not directly attached to the carbonyl through one of the following optionally substituted groups: —N—, —O—, triazole, or an amino acid;

wherein R$_8$ is not directly attached to the amine through one of the following optionally substituted groups: —S(=O)(=O)—, or —C(=O)—; and wherein R$_7$ is not —CH$_2$—O-phenyl.

2. The compound of claim 1, wherein there are at least four atoms located between a heteroatom in -L$_1$-Cy-L$_2$- and the nitrogen to which R$_3$ is attached.

3. The compound of claim 1, wherein L$_1$ is a direct bond or an optionally substituted group selected from —C$_{1-20}$alkyl, —C$_{1-20}$alkenyl, and —C$_{1-20}$alkynyl; wherein said —C$_{1-20}$alkyl-, —C$_{1-20}$alkenyl-, and —C$_{1-20}$alkynyl- is optionally substituted with one or more R' groups, and wherein optionally one or more non-adjacent carbon atoms in said —C$_{1-20}$alkyl-, —C$_{1-20}$alkenyl-, or —C$_{1-20}$alkynyl- are replaced by O, NR", or S.

4. The compound of claim 3, wherein:
L$_1$ is a direct bond, —(C$_{1-6}$alkyl-O)$_n$—, or an optionally substituted group selected from —C$_{1-20}$alkyl, —C$_{1-20}$alkenyl, and —C$_{1-20}$alkynyl; wherein said —C$_{1-20}$alkyl-, —C$_{1-20}$alkenyl-, and —C$_{1-20}$alkynyl- is optionally substituted with one or more R' groups; and wherein n is an integer from 1 to 10.

5. The compound of claim 1, wherein R$_3$ is —C(=O)OR$_4$ or —S(=O)(=O)R$_6$.

6. The compound of claim 1 wherein
R$_4$, R$_5$, R$_6$, and R$_7$ are L$_1$-X-L$_2$-Det;
L$_1$ and L$_2$ are each independently a direct bond, —(C$_{1-6}$alkyl-O)$_n$—, or an optionally substituted group selected from —C$_{1-20}$alkyl, —C$_{1-20}$alkenyl, and —C$_{1-20}$alkynyl; wherein said —C$_{1-20}$alkyl-, —C$_{1-20}$alkenyl-, and —C$_{1-20}$alkynyl- is optionally substituted with one or more R' groups; and wherein optionally one carbon atoms in said —C$_{1-20}$alkyl-, —C$_{1-20}$alkenyl-, or —C$_{1-20}$alkynyl- is replaced by O, NR", S;
X is selected from a direct bond, cycloalkyl, heterocyclyl, aryl, heteroaryl, C(=O), C(=O)O, OC(=O), S(=O), S(=O)(=O), C(=O)NR", NR"C(=O), NR"C(=O)O, OC(=O)NR", NR"SO$_2$, SO$_2$NR", NR"C(=O)NR", NR"S(=O)NR", or NR"S(=O)(=O)NR"; wherein said cycloalkyl, heterocyclyl, aryl, and heteroaryl is optionally substituted with one or more R' groups;
wherein n is an integer from 1 to 10.

7. The compound of claim 1, wherein Det is hydrogen.

8. The compound of claim 7, wherein L$_2$ is a direct bond and Det is hydrogen.

9. The compound of claim 1, wherein Det is a detectable label.

10. A pharmaceutical composition comprising the compound of claim 1 and one or more pharmaceutically acceptable carriers.

11. A compound or a stereoisomer, tautomer, racemic, or salt thereof, selected from:
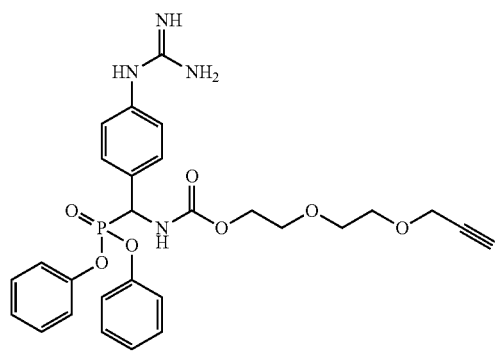
27
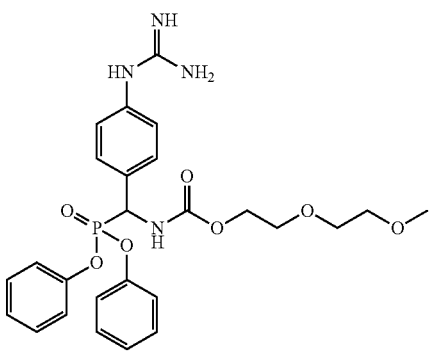
28
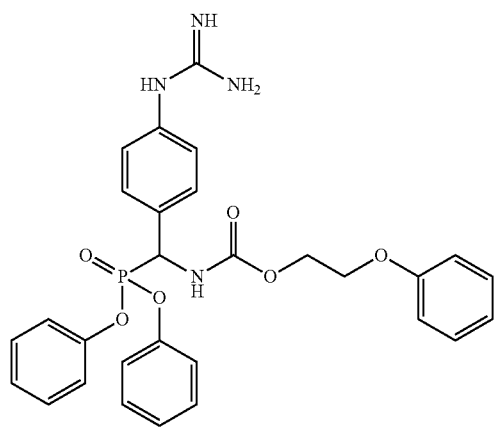
30
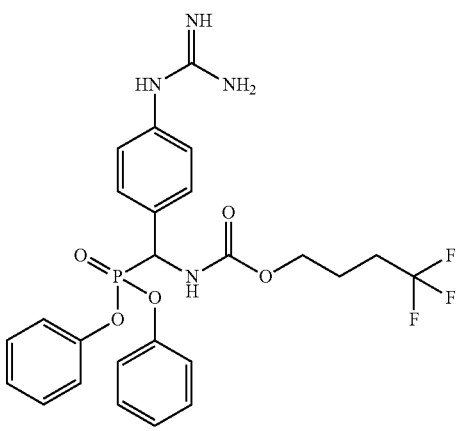
107
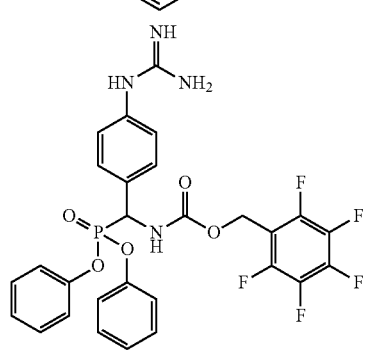
109
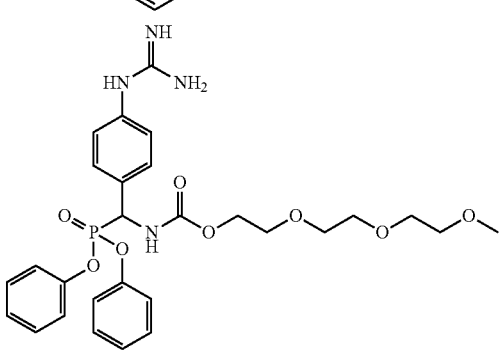
110
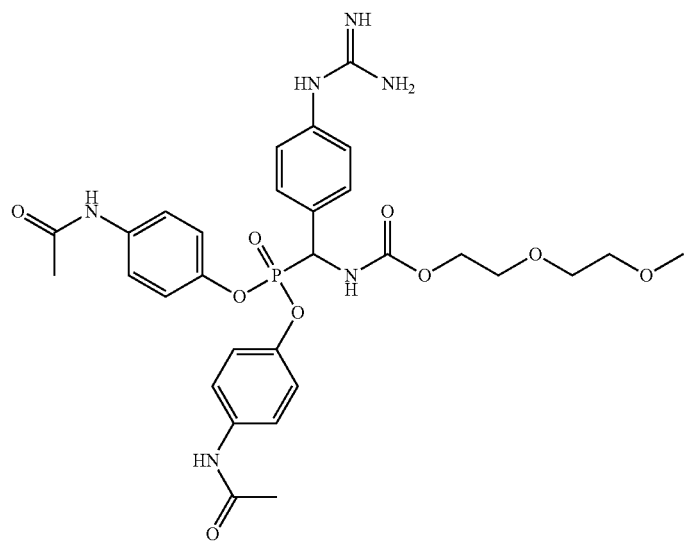
114

133
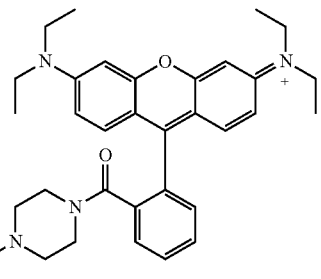
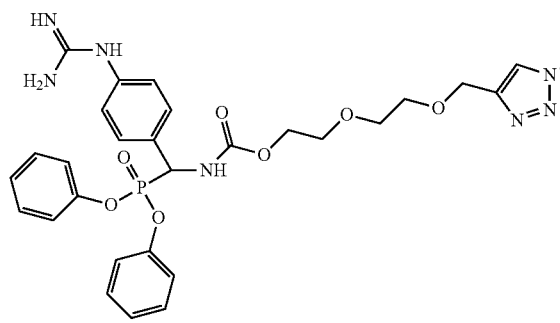
134
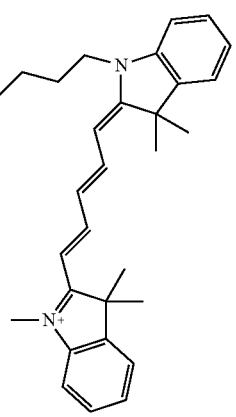
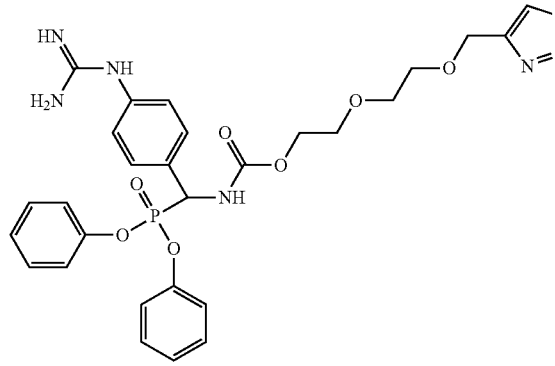
135
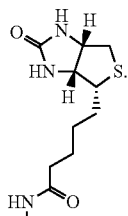
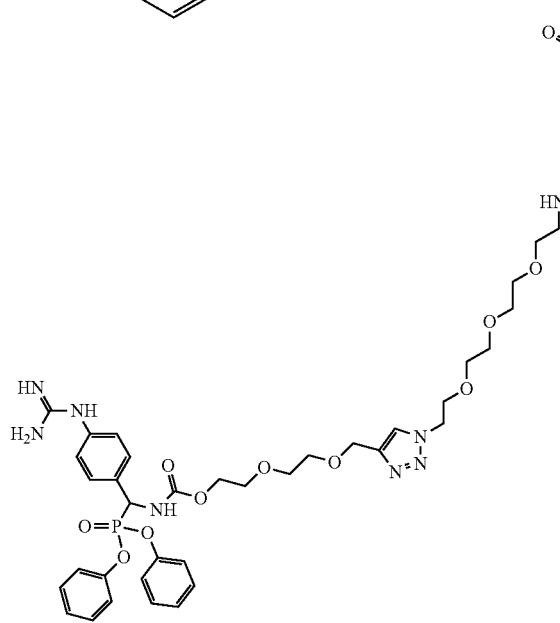
* * * * *